(12) United States Patent
Fukuda et al.

(10) Patent No.: US 10,813,621 B2
(45) Date of Patent: Oct. 27, 2020

(54) ANALYZER

(71) Applicant: Canon Medical Systems Corporation, Otawara-shi (JP)

(72) Inventors: Shogo Fukuda, Kawasaki (JP); Willem Gorissen, Zilverstraat Zoetermeer (NL); Joel Mancina, Tustin, CA (US); Gilles Daniel Joseph Guenette, Vernon Hills, IL (US); Hiroyuki Ouchi, Sapporo (JP); Shunsuke Satoh, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 649 days.

(21) Appl. No.: 15/449,020

(22) Filed: Mar. 3, 2017

(65) Prior Publication Data

US 2017/0252000 A1 Sep. 7, 2017

(30) Foreign Application Priority Data

Mar. 4, 2016 (JP) .................................. 2016-042372
Mar. 3, 2017 (JP) .................................. 2017-040239

(51) Int. Cl.
*A61B 8/08* (2006.01)
*A61B 8/06* (2006.01)
(Continued)

(52) U.S. Cl.
CPC .......... *A61B 8/0883* (2013.01); *A61B 5/0402* (2013.01); *A61B 5/7292* (2013.01);
(Continued)

(58) Field of Classification Search
CPC ............ A61B 2576/023; A61B 5/0402; A61B 5/7292; A61B 5/7485; A61B 8/06;
(Continued)

(56) References Cited

U.S. PATENT DOCUMENTS

| 8,626,279 B2 | 1/2014 | Edvardsen et al. | |
| 2015/0018684 A1* | 1/2015 | Abe ........................ | A61B 8/14 600/443 |
| 2015/0038846 A1* | 2/2015 | Abe ........................ | A61B 8/06 600/443 |

OTHER PUBLICATIONS

Bansal et al., How do I do it? Speckle-tracking echocardiography, 2013, Indian Heart Journal (Year: 2013).*

(Continued)

*Primary Examiner* — Bo Joseph Peng
(74) *Attorney, Agent, or Firm* — Oblon, McClelland, Maier & Neustadt, L.L.P.

(57) ABSTRACT

An analyzer in an embodiment includes processing circuitry. The processing circuitry identifies at least a part of a contour of a heart of a subject for an image corresponding to a first cardiac time phase and an image corresponding to a second cardiac time phase that are included in time-series images including the heart of the subject. The processing circuitry calculates, using the information about the identified contours, a first cardiac function parameter representing at least one of a volume or an ejection fraction of a heart chamber and a second cardiac function parameter representing a global strain of a myocardium corresponding to the heart chamber. The processing circuitry causes the first cardiac function parameter and the second cardiac function parameter to be displayed by common operation.

16 Claims, 11 Drawing Sheets

(51) Int. Cl.
    *A61B 5/0402*     (2006.01)
    *A61B 5/00*     (2006.01)

(52) U.S. Cl.
    CPC ............... *A61B 8/06* (2013.01); *A61B 8/488* (2013.01); *A61B 5/7485* (2013.01); *A61B 2576/023* (2013.01)

(58) Field of Classification Search
    CPC ....... A61B 8/0883; A61B 8/488; A61B 8/483; A61B 8/485; A61B 5/7289
    See application file for complete search history.

(56) References Cited

OTHER PUBLICATIONS

Mor-Avi et al., Current and Evolving Echocardiographic Techniques for the Quantitative Evaluation of Cardiac Mechanics, 2011 (Year: 2011).*

* cited by examiner

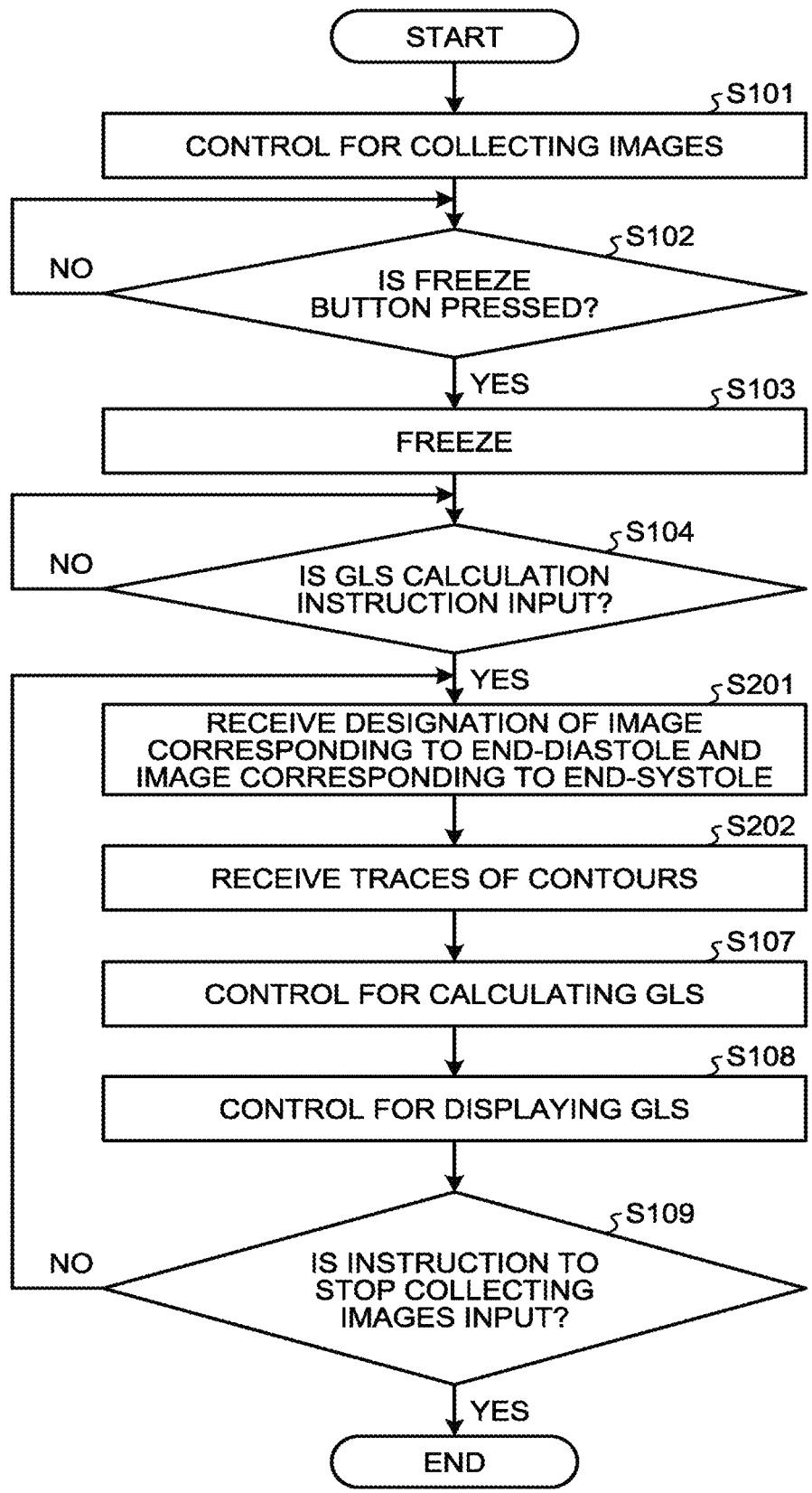

ANALYZER

CROSS-REFERENCE TO RELATED APPLICATIONS

This application is based upon and claims the benefit of priority from Japanese Patent Application No. 2016-042372, filed on Mar. 4, 2016; and Japanese Patent Application No. 2017-040239, filed on Mar. 3, 2017; the entire contents of which are incorporated herein by reference.

FIELD

Embodiments described herein relate generally to an analyzer.

BACKGROUND

There have been ultrasound diagnostic apparatuses that calculate, from reflected waves of ultrasound waves, myocardial strain indicators as cardiac function parameters having usefulness for diagnosis of cardiac diseases such as disease state elucidation, therapeutic effect determination, and prognosis estimation of various cardiac diseases. Among such myocardial strain indicators, a global longitudinal strain (GLS) is frequently used as an indicator for quantification of cardiac functions.

BRIEF DESCRIPTION OF THE DRAWINGS

FIG. 9 is a flowchart illustrating an exemplary flow of processing performed by the ultrasound diagnostic apparatus according to a fifth modification of the first embodiment;

DETAILED DESCRIPTION

An analyzer in each embodiment includes processing circuitry. The processing circuitry identifies a contour of at least a part of the heart of a subject for an image corresponding to a first cardiac time phase and an image corresponding to a second cardiac time phase that are included in time-series images including the heart of the subject. The processing circuitry calculates, using information about the identified contours, a first cardiac function parameter representing at least one of a volume and an ejection fraction of a heart chamber, and a second cardiac function parameter representing a global strain of a myocardium corresponding to the heart chamber. The processing circuitry causes the first cardiac function parameter and the second cardiac function parameter to be displayed by common operation.

The following describes an ultrasound diagnostic apparatus including a main body serving as the analyzer according to each of the embodiments with reference to the accompanying drawings. The embodiments can be appropriately combined.

First Embodiment

Figure 1:
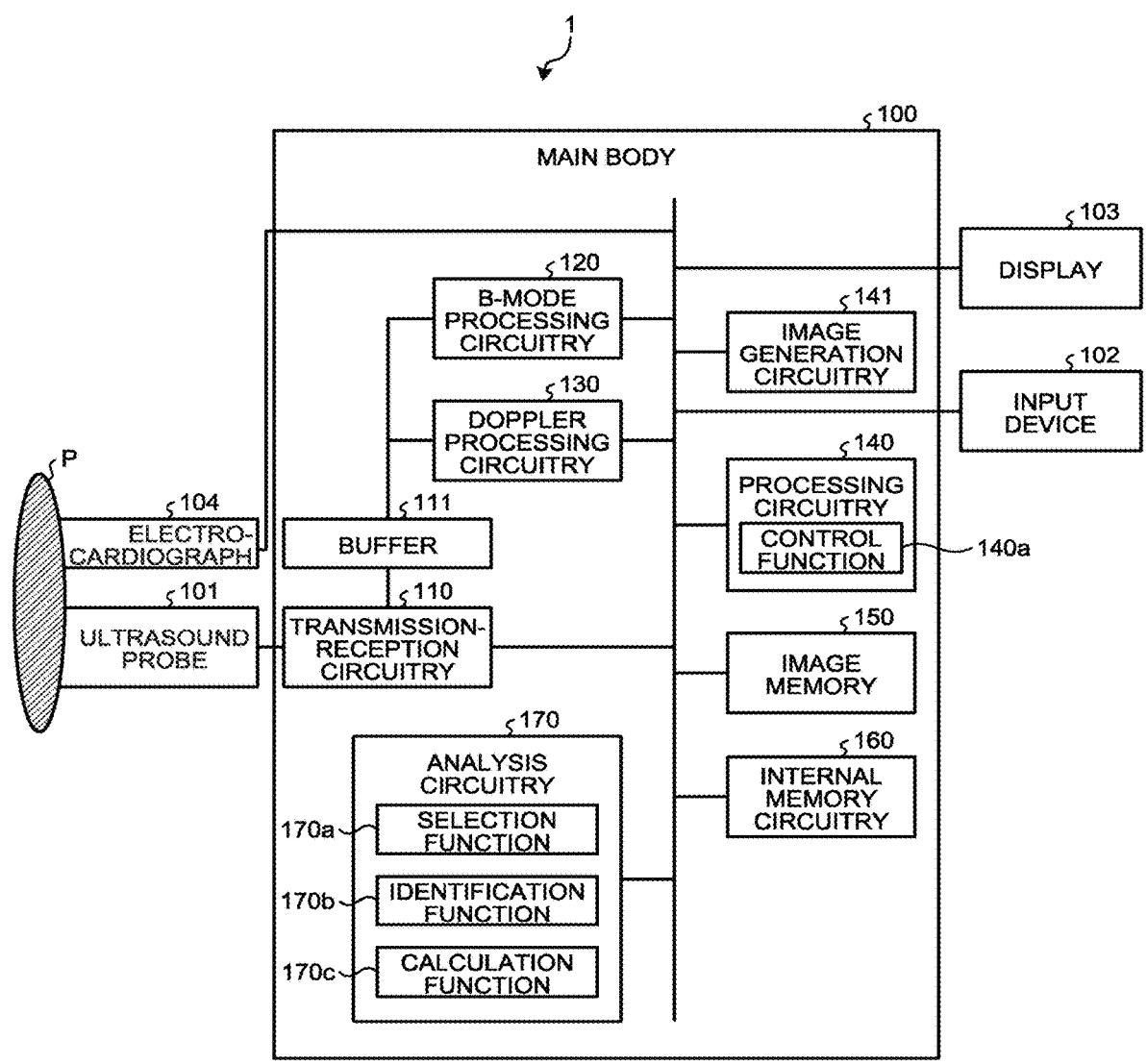
FIG. 1 is a block diagram illustrating an exemplary structure of an ultrasound diagnostic apparatus according to a first embodiment.

FIG. 1 is a block diagram illustrating an exemplary structure of the ultrasound diagnostic apparatus according to a first embodiment. As illustrated in FIG. 1, this ultrasound diagnostic apparatus 1 according to the first embodiment includes an ultrasound probe 101, an input device 102, a display 103, an electrocardiograph 104, and a main body 100. The ultrasound probe 101, the input device 102, the display 103, and the electrocardiograph 104 are connected to the main body 100 so as to enable communication with each other. A subject P does not belong to the ultrasonic diagnostic apparatus 1.

The ultrasound probe 101 transmits and receives ultrasound waves. The ultrasound probe 101 includes a plurality of transducer elements. The transducer elements generate ultrasound waves on the basis of drive signals supplied from transmission-reception circuitry 110 included in the main body 100, which is described later. The transducer elements included in the ultrasound probe 101 receive reflected waves from the subject P and convert the reflected waves into electrical signals. The ultrasound probe 101 includes a matching layer provided to the transducer elements and a backing material preventing ultrasound waves from propagating backward from the transducer elements, for example. The ultrasound probe 101 is connected to the main body 100 in a detachable manner.

Ultrasound waves transmitted from the ultrasound probe 101 to the subject P are reflected by a discontinuous surface of acoustic impedance in body tissues of the subject P one after another, and received by the multiple transducer elements included in the ultrasound probe 101 as reflected wave signals. The amplitudes of the received reflected wave signals depend on differences in acoustic impedance of the discontinuous surfaces where ultrasound waves are reflected. The reflected wave signals of the transmitted ultrasound pulses reflected by moving bloodstream and a surface of a cardiac wall change in frequency depending on velocity components of the moving object in the ultrasound wave transmission direction by a Doppler effect.

To the ultrasound probe 101 according to the first embodiment, a one-dimensional (1D) array probe that scans a two-dimensional region, and a fourth-dimensional (4D) array probe and two-dimensional (2D) array probe that scan a three-dimensional region are applicable. When scanning the two-dimensional region, the ultrasound probe 101 receives two-dimensional reflected wave signals. When scanning the three-dimensional region, the ultrasound probe 101 receives three-dimensional reflected wave signals.

The input device 102 includes devices such as a mouse, a keyboard, a button, a panel switch, a touch command screen, a foot switch, a trackball, a joystick, and a freeze button. The input device 102 receives various setting requests from a user of the ultrasound diagnostic apparatus 1 and transfers the received various setting requests to the main body 100. The input device 102 is an example of an operation unit.

The display 103 displays a graphical user interface (GUI) allowing the user of the ultrasound diagnostic apparatus 1 to input various setting requests using the input device 102, and a B mode image and a color Doppler image that are generated by the main body 100, for example. The display 103 is achieved by a liquid crystal monitor, a cathode ray tube (CRT) monitor, or a touch panel, for example.

The electrocardiograph 104 acquires an electrocardiogram (ECG) of the subject P as a biosignal of the subject P. The electrocardiograph 104 transmits the acquired electrocardiogram to the main body 100.

The main body 100 generates ultrasound image data on the basis of the reflected wave signals received by the ultrasound probe 101. The main body 100 illustrated in FIG. 1 generates two-dimensional ultrasound image data on the basis of the two-dimensional reflected wave signals or three-dimensional ultrasound image data on the basis of the three-dimensional reflected wave signals.

As exemplarily illustrated in FIG. 1, the main body 100 includes the transmission-reception circuitry 110, a buffer 111, B-mode processing circuitry 120, Doppler processing circuitry 130, processing circuitry 140, image generation circuitry 141, an image memory 150, internal memory circuitry 160, and analysis circuitry 170. The transmission-reception circuitry 110, the B-mode processing circuitry 120, the Doppler processing circuitry 130, the processing circuitry 140, the image memory 150, the internal memory circuitry 160, and the analysis circuitry 170 are connected so as to enable communication one with another.

The transmission-reception circuitry 110 includes a pulse generator, transmission delay circuitry, and a pulser, for example, and supplies the drive signals to the ultrasound probe 101. The pulse generator repeatedly generates rate pulses for the formation of transmission ultrasound waves at a certain repetition frequency (a pulse repetition frequency: PRF). The transmission delay circuitry provides, to each rate pulse generated by the pulse generator, a delay time for each transducer element necessary to converge ultrasound waves generated by the ultrasound probe 101 to a beam shape and to determine transmission directivity. The pulser applies drive signals (drive pulses) to the ultrasound probe 101 at timing based on the rate pulses. The transmission delay circuitry adjusts the transmission direction of ultrasound waves transmitted from the surfaces of the transducer elements to any direction by changing the delay time provided to each rate pulse.

The transmission-reception circuitry 110 has a function that can instantly change a transmission frequency and a transmission drive voltage for performing a certain scan sequence on the basis of an instruction from the processing circuitry 140. Particularly, the change of the transmission drive voltage is achieved by a mechanism that electrically switches linear amplifier oscillation circuitries that can instantly switch the voltage or a plurality of power source units.

The transmission-reception circuitry 110 includes amplification circuitry, an analog to digital (A/D) converter, reception delay circuitry, an adder, and an orthogonal detector, for example. The transmission-reception circuitry 110 generates reflected wave data (echo data) by performing various types of processing on the reflected wave signals received by the ultrasound probe 101. The transmission-reception circuitry 110 generates two-dimensional reflected wave data on the basis of the two-dimensional reflected wave signals. The transmission-reception circuitry 110 generates three-dimensional reflected wave data on the basis of the three-dimensional reflected wave signals.

The amplification circuitry amplifies the reflected wave signals for each channel to perform gain correction processing. The A/D converter A/D converts the gain corrected reflected wave signals. The reception delay circuitry provides the digital data with the reception delay times necessary to determine the reception directivity. The adder performs addition processing on the reflected wave signals to which the reception delay times are provided by the reception delay circuitry. The addition processing performed by the adder enhances the deflection components from the direction corresponding to the reception directivity of the reflected wave signals.

The orthogonal detector converts the output signal of the adder into an in-time phase signal (an I signal) and an orthogonal (quadrature-time phase) signal (a Q signal) in a baseband. The orthogonal detector stores the I signal and the Q signal (hereinafter described as the IQ signal) in the buffer 111 as the reflected wave data. The orthogonal detector may convert the output signal of the adder into a radio frequency (RF) signal and thereafter store the RF signal in the buffer 111. The IQ signal and the RF signal are reception signals that include phase information.

The buffer 111 temporarily stores therein the reflected wave data (the IQ signal) generated by the transmission-reception circuitry 110. Specifically, the buffer 111 stores therein the IQ signals corresponding to several frames or the IQ signals corresponding to several volumes. The buffer 111 is a first-in/first-out (FIFO) memory, for example, and stores therein the IQ signals corresponding to a predetermined number of frames. When the IQ signal of one frame is newly generated by the transmission-reception circuitry 110, the buffer 111 destroys the IQ signal of one frame, the generated time of the IQ signal being the oldest, and stores therein the newly generated IQ signal of one frame, for example. The buffer 111 is connected to the transmission-reception circuitry 110, the B-mode processing circuitry 120, and the Doppler processing circuitry 130 so as to enable communication with each other.

The B-mode processing circuitry 120 and the Doppler processing circuitry 130 are each achieved by a processor, for example. The B-mode processing circuitry 120 and the Doppler processing circuitry 130 perform various types of signal processing on the reflected wave data generated by the transmission-reception circuitry 110 from the reflected wave signals. The B-mode processing circuitry 120 reads the reflected wave data from the buffer 111 and performs logarithm amplification, envelope detection processing, and logarithm compression on the read reflected wave data to generate B-mode data in which a signal intensity is expressed by luminance for each of a number of points. The B-mode processing circuitry 120 generates two-dimensional B-mode data from the two-dimensional reflected wave data. The B-mode processing circuitry 120 generates three-dimensional B-mode data from the three-dimensional reflected wave data.

The Doppler processing circuitry 130 performs frequency analysis on the reflected wave data read from the buffer 111 to generate Doppler data in which movement information about a moving object in a scan range based on the Doppler effect is extracted. Specifically, the Doppler processing circuitry 130 generates the Doppler data in which an average speed, an average dispersion value, and the like are estimated as the movement information about the moving object for each of multiple sample points. The moving object is a bloodstream, a tissue of a cardiac wall, or a contrast agent, for example. The bloodstream is a bloodstream in a heart chamber, or a bloodstream in a cardiac wall, for example. The Doppler processing circuitry 130 according to the embodiment generates the Doppler data in which an average speed of a bloodstream, an average dispersion value of the bloodstream, and the like are estimated as the movement information (bloodstream information) about the bloodstream for each of multiple sample points. The Doppler processing circuitry 130 generates the two-dimensional Doppler data from the two-dimensional reflected wave data. The Doppler processing circuitry 130 generates the three-dimensional Doppler data from the three-dimensional reflected wave data.

The image generation circuitry 141 is achieved by a processor, for example. The image generation circuitry 141 generates ultrasound images from the data generated by the B-mode processing circuitry 120 and the Doppler processing circuitry 130. Specifically, the image generation circuitry 141 generates a two-dimensional B-mode image in which an intensity of the reflected wave is expressed by luminance from the two-dimensional B-mode data generated by the B-mode processing circuitry 120. The image generation circuitry 141 generates a two-dimensional Doppler image in which the bloodstream information is imaged from the two-dimensional Doppler data generated by the Doppler processing circuitry 130. The two-dimensional Doppler image is an image of a velocity image, a distribution image, or an image of the combination of these images. The image generation circuitry 141 generates color Doppler image data displaying the bloodstream information with colors or Doppler image data displaying one piece of bloodstream information with a gray scale.

The image generation circuitry 141 generally generates the ultrasound image data for display by converting (scan converting) a scanning line signal string for ultrasound scanning into a scanning line signal string in a video format typified by a TV format. Specifically, the image generation circuitry 141 generates the ultrasound image data for display by coordinate transformation in accordance with the ultrasound scanning manner by the ultrasound probe 101. The image generation circuitry 141 performs various types of image processing beside the scan conversion. For example, the image generating circuitry 141 performs image processing (smoothing processing) in which an image of average luminance is regenerated using a plurality of image frames after scan conversion or image processing (edge enhancement processing) in which a differential filter is used in an image. The image generation circuitry 141 combines character information including various parameters, a scale, and a body mark, for example, with the ultrasound image data.

The B-mode data and the Doppler data are the ultrasound image data before the scan conversion processing. The data generated by the image generation circuitry 141 is the ultrasound data for display after the scan conversion processing. The B-mode data and the Doppler data are also called raw data.

Furthermore, the image generation circuitry 141 generates a three-dimensional B-mode image by performing coordinate transformation on the three-dimensional B-mode data generated by the B-mode processing circuitry 120. The image generation circuitry 141 generates a three-dimensional Doppler image by performing coordinate transformation on the three-dimensional Doppler data generated by the Doppler processing circuitry 130.

Furthermore, the image generation circuitry 141 performs rendering processing on the volume data for producing various two-dimensional images used for displaying the volume data on the display 103. One of the rendering processing performed by the image generation circuitry 141 is processing in which a multi-planar reconstruction (MPR) image is generated from the volume data by an MPR technique. Another one of the rendering processing performed by the image generation circuitry 141 is volume rendering (VR) processing in which the two-dimensional image is generated by reflecting three-dimensional information.

The image generation circuitry 141 stores the ultrasound image data for display and a time at which the ultrasound scanning is performed for producing the ultrasound image data in the image memory 150 in association with an electrocardiogram transmitted from the electrocardiograph 104. As a result, a selection function 170a, which is described later, can acquire the ultrasound image data at a certain cardiac time phase by referring to the data stored in the image memory 150.

The processing circuitry 140 is achieved by a processor, for example. The processing circuitry 140 includes a control function 140a. The control function 140a, which is the component of the processing circuitry 140 illustrated in FIG. 1, is recorded in the internal memory circuitry 160 as a computer executable program, for example. The processing circuitry 140 reads the program from the internal memory circuitry 160 and executes the read program, thereby achieving the function corresponding to the program. In other words, the processing circuitry 140 after reading the program has the control function 140a. The control function 140a in the embodiment is an example of a controller.

The control function 140a controls the whole processing of the ultrasound diagnostic apparatus 1. For example, the control function 140a controls the processing performed by the transmission-reception circuitry 110, the B-mode processing circuitry 120, the Doppler processing circuitry 130, and the selection function 170a, an identification function 170b, and a calculation function 170c, which are described later, of the analysis circuitry 170 on the basis of various instructions input by the user via the input device 102, and the various control programs and various types of data read from the internal memory circuitry 160. The control function 140a controls the display 103 such that the display 103 displays the ultrasound images for display stored in the image memory 150 and the internal memory circuitry 160.

The control function 140a controls ultrasound scanning by controlling the ultrasound probe 101 via the transmission-reception circuitry 110, for example.

The analysis circuitry 170 includes the selection function 170a, the identification function 170b, and the calculation function 170c. Each processing function of the selection function 170a, the identification function 170b, and the calculation function 170c, which are the components of the analysis circuitry 170 illustrated in FIG. 1, is recorded in the internal memory circuitry 160 as a computer executable program, for example. The analysis circuitry 170 is a processor that reads each program from the internal memory circuitry 160 and executes the read program, thereby achieving the function corresponding to the program. In other words, the analysis circuitry 170 after reading the respective programs has the respective functions illustrated in the analysis circuitry 170 illustrated in FIG. 1. The selection function 170a in the embodiment is an example of a selection unit. The identification function 170b is an example of an identification unit. The calculation function 170c is an example of a calculation unit. The various types of processing executed by the selection function 170a, the identification function 170b, and the calculation function 170c are described later.

In the embodiment, the term "processor" means a central processing unit (CPU), a graphical processing unit (GPU), an application specific integrated circuit (ASIC), or a circuitry of a programmable logic device such as a simple programmable logic device (SPLD), a complex programmable logic device (CPLD), or a field programmable gate array (FPGA). The processor reads the program stored in the internal memory circuitry 160 and executes the program to achieve the function. The program may be directly built in the circuitry of the processor instead of storing the program in the internal memory circuitry 160. In this case, the processor reads the program built in the circuitry and executes the read program to achieve the function. Each processor in the embodiment may be achieved as single circuitry. A plurality of independent circuitries may be combined as a single processor and the single processor may achieve the functions of the respective processors.

The image memory 150 stores therein the ultrasound image data for display generated by the image generation circuitry 141. The image memory 150 can also store therein the B-mode data generated by the B-mode processing circuitry 120 and the Doppler data generated by the Doppler processing circuitry 130. The B-mode data and the Doppler data stored by the image memory 150 can be called by the user after diagnosis, for example. The data is retrieved via the image generation circuitry 141 and served as the ultrasound image data for display. The image memory 150 can also store therein the reflected wave data output by the transmission-reception circuitry 110.

The internal memory circuitry 160 stores therein a control program for ultrasound transmission and reception, image processing, and display processing, diagnosis information (e.g., a patient's ID, and a doctor's observation), and various types of data such as diagnosis protocols and various body marks. The internal memory circuitry 160 is also used for storing the ultrasound images generated by the image generation circuitry 141, for example, as needed. The data stored in the internal memory circuitry 160 can be transferred to external apparatuses via an Interface, which is not illustrated. The internal memory circuitry 160 can also store therein data transferred from the external apparatuses via the interface, which is not illustrated. The internal memory circuitry 160 stores therein data used when the selection function 170a, the identification function 170b, and the calculation function 170c perform various types of processing and data calculated as the results of the various types of processing. For example, the internal memory circuitry 160 stores therein information about the contour identified by the identification function 170b. The information about the contour is described later. The internal memory circuitry 160 stores therein the information about the contour (e.g., a position of the contour in the image). The internal memory circuitry 160 may store therein the information about the contour for each cross section. The internal memory circuitry 160 is an example of the memory circuitry.

The whole structure of the ultrasound diagnostic apparatus 1 according to the first embodiment is described as above.

The following describes an exemplary case where the ultrasound diagnostic apparatus calculates a longitudinal strain in the longitudinal direction for each of 18 segments in the left ventricle of a heart using a speckle tracking method, and calculates an average of the calculated strains in the longitudinal direction as a global longitudinal strain (GLS).

In this case, the user, such as a doctor, operates the input device so as to cause the display to display one of the time-series B-mode images of the longitudinal cross section of the heart generated by the ultrasound diagnostic apparatus. The user, then, sets the contour of the myocardium of the left ventricle in the B-mode image displayed on the display. The user operates the input device so as to input, to the main body, an instruction to start the speckle tracking that traces a point on the contour of the myocardium over a plurality of frames. The user checks, for each frame, the tracking result of the point on the contour of the myocardium over the multiple frames displayed on the display, and corrects the point on the contour of the myocardium while operating the input device when the tracking result is wrong. The user operates the input device so as to input, to the main body, an instruction to calculate the GLS. The user checks the GLS at each cardiac time phase, which is calculated by the main body and displayed on the display, and performs diagnosis of cardiac diseases.

When the ultrasound diagnostic apparatus calculates the GLS using the speckle tracking method as described above, the user needs time to operate the input device relatively many times, and thus the user feels troublesome in operating the apparatus. It is, thus, difficult to easily perform diagnosis of cardiac diseases when the ultrasound diagnostic apparatus calculates the GLS using the speckle tracking method.

The ultrasound diagnostic apparatus 1 according to the first embodiment allows the user to easily perform diagnosis of cardiac diseases by the processing described below.

Figure 2:
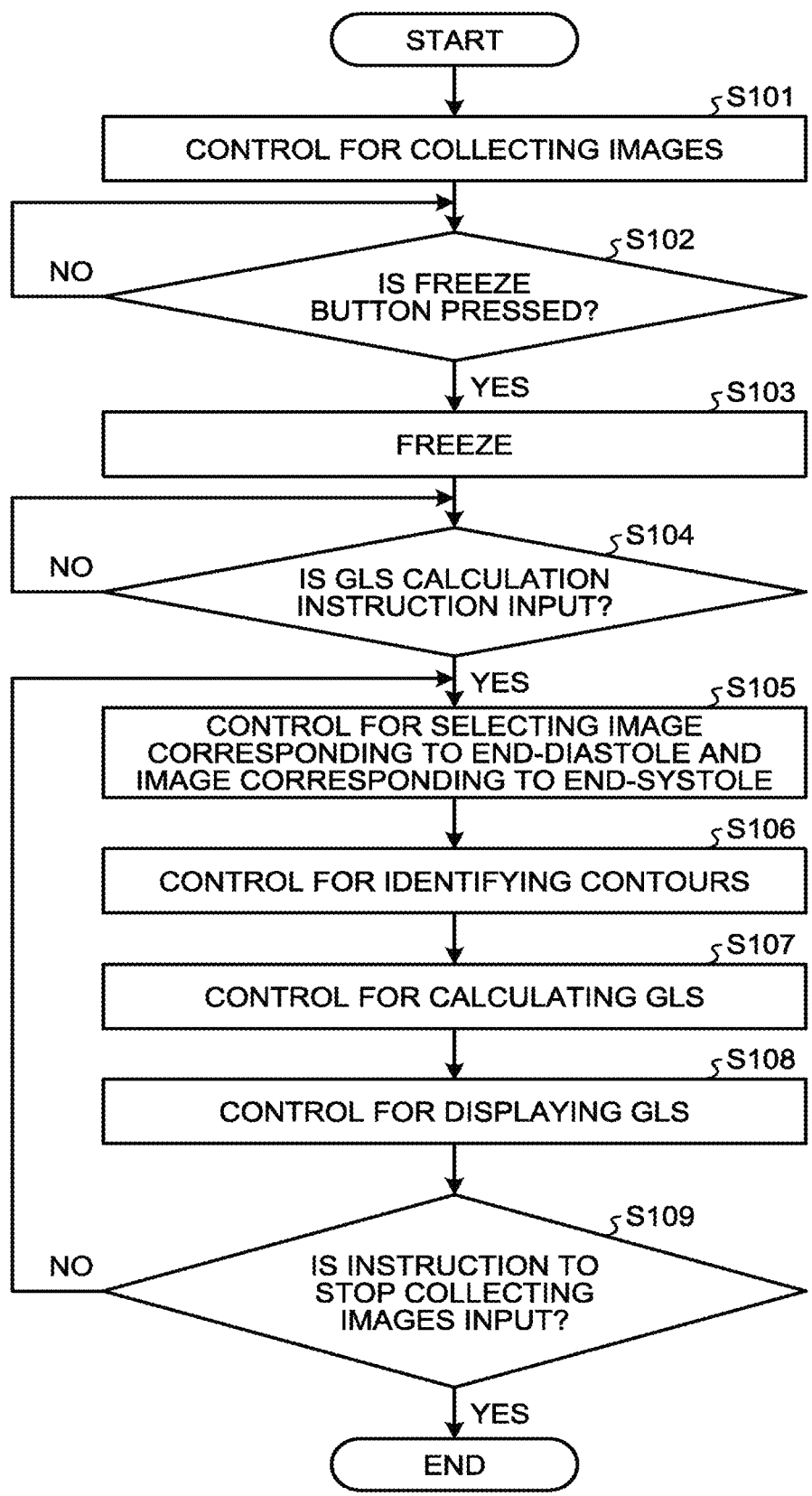
FIG. 2 is a flowchart illustrating an exemplary flow of processing performed by the ultrasound diagnostic apparatus according to the first embodiment.

FIG. 2 is a flowchart illustrating an exemplary flow of the processing performed by the ultrasound diagnostic apparatus 1 according to the first embodiment. The processing exemplarily illustrated in FIG. 2 is performed when the user operates the input device 102 and an instruction to start collection of images including the heart of the subject P is input from the input device 102, for example.

As exemplarily illustrated in FIG. 2, at step S101, the control function 140a of the processing circuitry 140 controls the respective circuitries so as to collect images including the heart of the subject P, such as the longitudinal cross section images and volume data. At step S101, the control function 140a controls the transmission-reception circuitry 110 such that the transmission-reception circuitry 110 causes the ultrasound probe 101 to start the transmission of ultrasound waves, and starts producing the reflected wave data by performing the various types of processing on the received reflected wave signals. When the two-dimensional scanning is performed, the user operates the ultrasound probe 101 such that the longitudinal cross section of the heart of the subject P is scanned. When the three-dimensional scanning is performed, the user operates the ultrasound probe 101 such that a three-dimensional region of the heart of the subject P is scanned. When the two-dimensional scanning is performed, the transmission-reception circuitry 110 sequentially generates the two-dimensional reflected wave data on the basis of the two-dimensional reflected wave signals sequentially received as a result of the scanning of the longitudinal cross section, and starts sequentially storing the generated two-dimensional reflected wave data in the buffer 111. When the three-dimensional scanning is performed, the transmission-reception circuitry 110 sequentially generates the three-dimensional reflected wave data on the basis of the three-dimensional reflected wave signals sequentially received as a result of the scanning of the three-dimensional region including the heart, and starts sequentially storing the generated three-dimensional reflected wave data in the buffer 111.

At step S101, the control function 140*a* controls the B-mode processing circuitry 120 such that the B-mode processing circuitry 120 starts producing the time-series B-mode data. When the two-dimensional scanning is performed, the B-mode processing circuitry 120 sequentially generates the two-dimensional B-mode data using the two-dimensional reflected wave data stored in the buffer 111, and starts sequentially storing the generated time-series two-dimensional B-mode data in the image memory 150. When the three-dimensional scanning is performed, the B-mode processing circuitry 120 sequentially generates the three-dimensional B-mode data using the three-dimensional reflected wave data stored in the buffer 111, and starts sequentially storing the generated time-series three-dimensional B-mode data in the image memory 150.

At step S101, the control function 140*a* controls the image generation circuitry 141 such that the image generation circuitry 141 starts producing the time-series B-mode images. When the two-dimensional scanning is performed, the image generation circuitry 141 sequentially reads the B-mode data from the image memory 150 and starts sequentially producing the longitudinal cross-sectional images of the heart of the subject P from the read B-mode data. Types of longitudinal cross-sectional image are an apical four-chamber image (apical four-chamber cross-sectional image) visualizing four chambers of the heart, an apical three-chamber image (apical three-chamber cross-sectional image) visualizing three chambers of the heart, and an apical two-chamber image (apical two-chamber cross-sectional image) visualizing two chambers of the heart. The longitudinal cross-sectional image is the image including the heart of the subject P.

When the three-dimensional scanning is performed, the image generation circuitry 141 sequentially reads the B-mode data from the image memory 150 and starts sequentially producing the three-dimensional B-mode images (volume data) including the heart of the subject P from the read B-mode data. The volume data is the image including the heart of the subject P.

At step S101, when the two-dimensional scanning is performed, the image generation circuitry 141 starts sequentially storing each of the sequentially generated longitudinal cross-sectional images and a time at which the ultrasound scanning is performed for producing the longitudinal cross-sectional image in the image memory 150 in association with an electrocardiogram transmitted from the electrocardiograph 104. At step S101, when the three-dimensional scanning is performed, the image generation circuitry 141 starts sequentially storing each of the sequentially generated volume data and a time at which the ultrasound scanning is performed for producing the volume data in the image memory 150 in association with an electrocardiogram transmitted from the electrocardiograph 104.

At step S101, when the two-dimensional scanning is performed, the control function 140*a* starts causing the display 103 to display the longitudinal cross-sectional images stored in the image memory 150 in the time-series order.

When the three-dimensional scanning is performed, the control function 140*a* controls the image generation circuitry 141 such that image generation circuitry 141 starts sequentially producing surfaces A from the volume data and sequentially storing the generated surfaces A in the image memory 150. The control function 140*a* starts causing the display 103 to display the surfaces A sequentially generated by the image generation circuitry 141 in the time-series order. The image generation circuitry 141 starts storing each of the sequentially generated surfaces A, the volume data from which the surface A is generated, and a time at which the ultrasound scanning is performed for producing the surface A in the image memory 150 in association with an electrocardiogram transmitted from the electrocardiograph 104.

At step S101, when the two-dimensional scanning is performed, the control function 140*a* controls a data amount of the longitudinal cross-sectional images stored in the image memory 150 such that the longitudinal cross-sectional images in a certain time period from the present time to the past by a certain time are stored in the image memory 150. When the three-dimensional scanning is performed, the control function 140*a* controls a data amount of the volume data stored in the image memory 150 such that the volume data in a certain time period from the present time to the past by a certain time is stored in the image memory 150. For example, the control function 140*a* controls a data amount of the longitudinal cross-sectional images or the volume data stored in the image memory 150 such that the longitudinal cross-sectional images or the volume data in at least one cardiac beat (one cardiac period) is stored in the image memory 150.

The control function 140*a* determines whether the freeze button is pressed (step S102). If the freeze button is not pressed (No at step S102), the control function 140*a* performs the determination again at step S102.

If the freeze button is pressed (Yes at step S102), the control function 140*a* performs the processing described below at step S103. At step S103, the control function 140*a* causes the longitudinal cross-sectional image or the surface A displayed on the display 103 at timing when the freeze button is pressed to continue to be displayed without any change. The control function 140*a* freezes the display of the longitudinal cross-sectional image or the surface A. The longitudinal cross-sectional image or the surface A continues to be displayed until the longitudinal cross-sectional image corresponding to an end-diastole and the longitudinal cross-sectional image corresponding to an end-systole are displayed on the display 103 at step S105, which is described later.

At step S103, when the two-dimensional scanning is performed, the control function 140*a* acquires the longitudinal cross-sectional images corresponding to the certain time period stored in the image memory 150 at the timing when the freeze button is pressed. At step S103, when the three-dimensional scanning is performed, the control function 140*a* acquires the volume data that corresponds to the certain time period and is stored in the image memory 150 at the timing when the freeze button is pressed.

Figure 3:
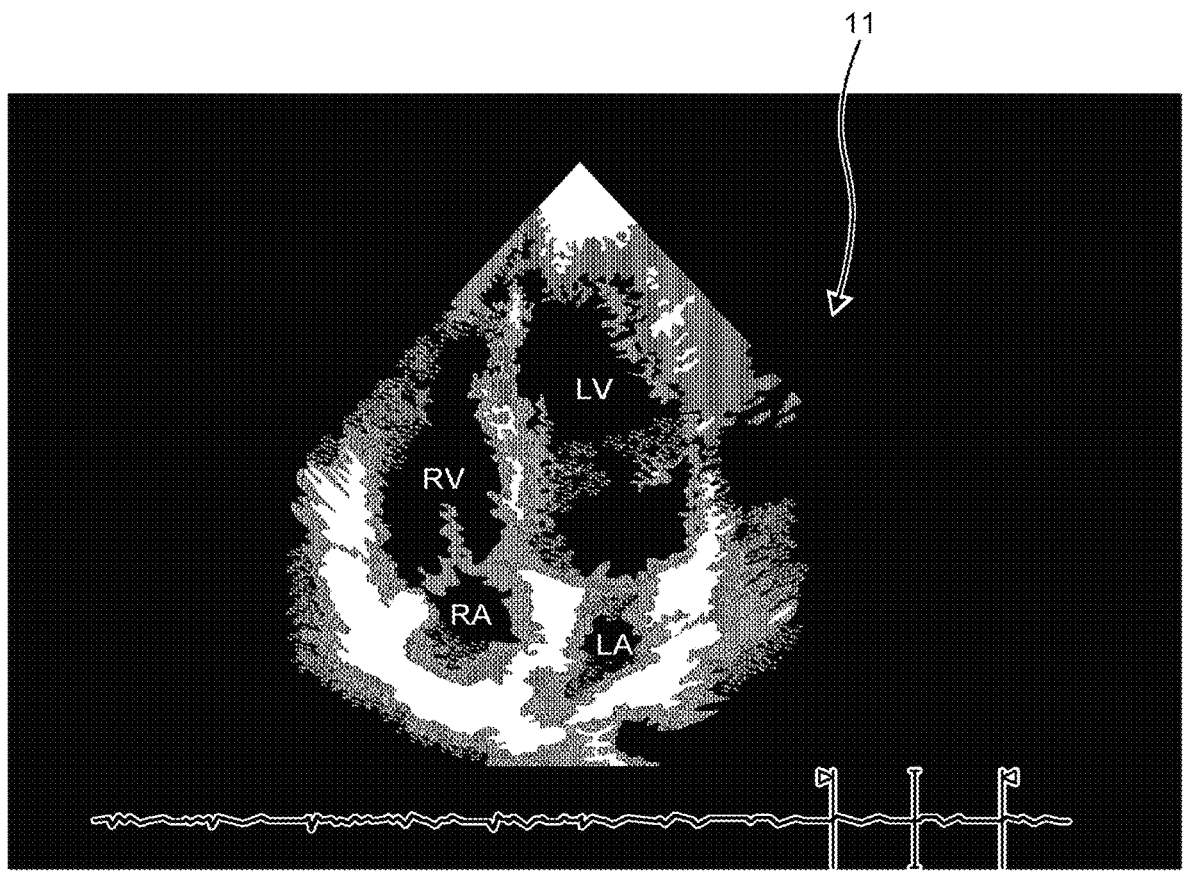
FIG. 3 is a diagram for explaining an example of processing performed by a control function according to the first embodiment.

FIG. 3 is a diagram for explaining an example of the processing performed by the control function 140*a* according to the first embodiment. As exemplarily illustrated in FIG. 3, when an apical four-chamber image 11 is displayed on the display 103 at timing when the freeze button is pressed, the control function 140a causes the apical four-chamber image 11 to continue to be displayed without any change. In FIG. 3, the apical four-chamber image 11 is illustrated in which a left ventricle (LV), a left atrium (LA), a right ventricle (RV), and a right atrium (RA) are visualized.

Referring back to FIG. 2, the control function 140a determines whether an instruction to automatically calculate the GLS (GLS calculation instruction) is input from the input device 102 by the user operating the input device 102 (step S104).

The following describes the GLS. The myocardial strain indicators are used as cardiac function parameters having usefulness for diagnosis of cardiac diseases, such as disease state elucidation, therapeutic effect determination, and prognosis estimation of various cardiac diseases. Among such myocardial strain indicators, the GLS is frequently used as an indicator for quantification of cardiac functions. The GLS is calculated using the following expression (1), for example.

$$GLS\ (\%) = [(L1-L0)/L0]*100 \qquad (1)$$

where "−" is the operator indicating subtraction, "/" is the operator indicating division, "*" is the operator indicating multiplication, L1 is the length of the contour of an endocardium or an epicardium of the left ventricle of the heart at a certain time phase (first time phase) in one cardiac beat, L0 is the length of the contour of the endocardium or the epicardium of the left ventricle of the heart at another time phase (second time phase) in one cardiac beat. The GLS is a value of a ratio of a value obtained by subtracting Lo, which is the length of the contour at the second time phase, from L1, which is the length of the contour at the first time phase, to Lo, and expressed by percent. The length of the contour in the left ventricle in the apical two-chamber image is the length of the contour from a mitral valve to an aortic valve via a cardiac apex because the mitral valve and the aortic valve are visualized in the apical two-chamber image. The length of the contour in the left ventricle in the apical three-chamber image is the length of the contour from the mitral valve to the aortic valve via the cardiac apex because the mitral valve and the aortic valve are visualized in the apical three-chamber image. The length of the contour in the left ventricle in the apical four-chamber image is the length of the contour from the mitral valve to the mitral valve via the cardiac apex because only the mitral valve is visualized out of the mitral valve and the aortic valve in the apical four-chamber image. The length of the contour in the left ventricle in the volume data is the length of the contour from the mitral valve to the aortic valve via the cardiac apex in the apical two-chamber cross section and the apical three-chamber cross section, and the length of the contour from the mitral valve to the mitral valve via the cardiac apex in the apical four-chamber cross section, for example.

It is particularly useful information for diagnosis of cardiac diseases to use the GLS obtained by applying the end-systole to the first time phase (first cardiac time phase) and the end-diastole to the second time phase (second cardiac time phase). The following, thus, describes a case where the end-systole is applied to the first time phase and the end-diastole is applied to the second time phase. Any time phase can be applied to the first time phase and the second time phase. In the following description, the first cardiac time phase corresponds to the end-systole while the second cardiac time phase corresponds to the end-diastole.

If no GLS calculation instruction is input (No at step S104), the control function 140a performs the processing again at step S104.

If the GLS calculation instruction is input (Yes at step S104), the control function 140a performs the processing described below at step S105. At step S105, when the two-dimensional scanning is performed, the control function 140a controls the selection function 170a such that the selection function 170a selects the longitudinal cross-sectional image corresponding to the end-diastole and the longitudinal cross-sectional image corresponding to the end-systole in one cardiac beat out of the longitudinal cross-sectional images that correspond to the certain time period and are acquired from the image memory 150 at step S103. The selection function 170a refers to the data that is stored in the image memory 150 and in which the longitudinal cross-sectional image, the ultrasound scanning time, and the electrocardiogram are in association with one another, and selects the longitudinal cross-sectional image corresponding to the end-diastole and the longitudinal cross-sectional image corresponding to the end-systole in one cardiac beat out of the time-series longitudinal cross-sectional images. The selection function 170a may select the longitudinal cross-sectional image corresponding to the end-diastole and the longitudinal cross-sectional image corresponding to the end-systole by setting an R wave to be the end-diastole and a T wave to be the end-systole. The selection function 170a may select, using other known techniques, the longitudinal cross-sectional image corresponding to the end-diastole and the longitudinal cross-sectional image corresponding to the end-systole in one cardiac beat out of the time-series longitudinal cross-sectional images.

At step S105, when the three-dimensional scanning is performed, the control function 140a controls the selection function 170a such that the selection function 170a selects the volume data corresponding to the end-diastole and the volume data corresponding to the end-systole in one cardiac beat out of the volume data that corresponds to the certain time period and is acquired from the image memory 150 at step S103. The selection function 170a refers to the data that is stored in the image memory 150 and in which the volume data, the ultrasound scanning time, the electrocardiogram, and the surface A are in association with one another, and selects the volume data corresponding to the end-diastole and the volume data corresponding to the end-systole in one cardiac beat out of the time-series volume data.

When the longitudinal cross-sectional image corresponding to the end-diastole and the longitudinal cross-sectional image corresponding to the end-systole are selected at step S105, the control function 140a causes the display 103 to display the selected longitudinal cross-sectional image corresponding to the end-diastole and longitudinal cross-sectional image corresponding to the end-systole.

When the volume data corresponding to the end-diastole and the volume data corresponding to the end-systole are selected at step S105, the control function 140a controls the image generation circuitry 141 such that the image generation circuitry 141 generates, by the MPR, the longitudinal cross-sectional image from each of the selected volume data corresponding to the end-diastole and volume data corresponding to the end-systole. The control function 140a causes the display 103 to display the longitudinal cross-sectional image corresponding to the end-diastole and the longitudinal cross-sectional image corresponding to the end-systole that are generated by the image generation circuitry 141.

Figure 4:
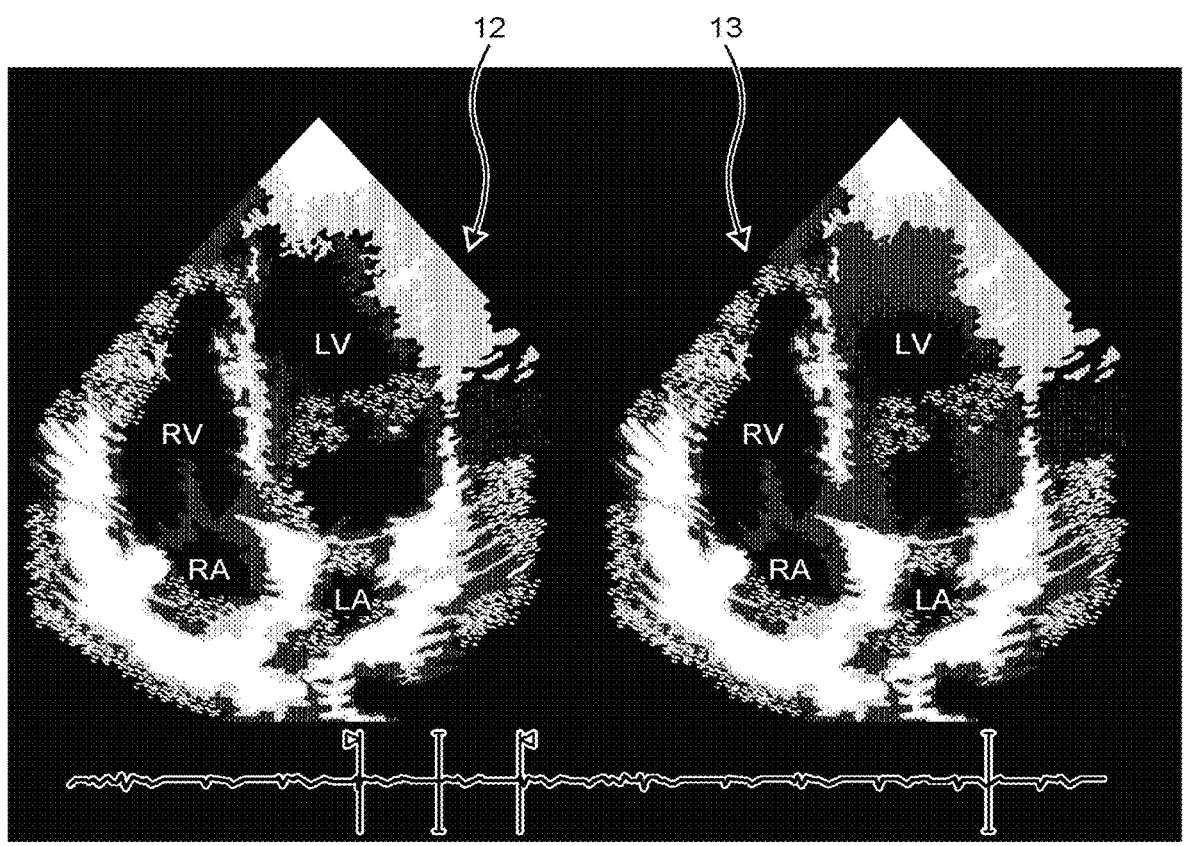
FIG. 4 is a diagram for explaining an example of processing performed by a selection function according to the first embodiment.

FIG. 4 is a diagram for explaining an example of the processing performed by the selection function 170a according to the first embodiment. At step S105, when the two-dimensional scanning is performed, the selection function 170a selects an apical four-chamber image 12 corresponding to the end-diastole and an apical four-chamber image 13 corresponding to the end-systole out of the time-series apical four-chamber images, for example. As exemplarily illustrated in FIG. 4, the selection function 170a causes the display 103 to display the selected apical four-chamber image 12 and apical four-chamber image 13.

At step S106, when the two-dimensional scanning is performed, the control function 140a controls the identification function 170b such that the identification function 170b automatically traces and identifies the two-dimensional contour of the heart for each of the selected longitudinal cross-sectional image corresponding to the end-diastole and longitudinal cross-sectional image corresponding to the end-systole. The identification function 170b identifies the contour from the mitral valve to the mitral valve via the cardiac apex as the contour of the left ventricle of the heart when the longitudinal cross-sectional image is the apical four-chamber image, for example. The identification function 170b identifies the contour from the mitral valve to the aortic valve via the cardiac apex as the contour of the left ventricle of the heart when the longitudinal cross-sectional image is the apical three-chamber image, for example. The identification function 170b identifies the contour from the mitral valve to the aortic valve via the cardiac apex as the contour of the left ventricle of the heart when the longitudinal cross-sectional image is the apical two-chamber image, for example.

At step S106, when the three-dimensional scanning is performed, the control function 140a controls the identification function 170b such that identification function 170b automatically traces and identifies the three-dimensional contour of the heart for each of the selected volume data corresponding to the end-diastole and volume data corresponding to the end-systole. The identification function 170b identifies the three-dimensional contour of the left ventricle of the heart for each of the selected volume data corresponding to the end-diastole and volume data corresponding to the end-systole.

When the three-dimensional scanning is performed, the identification function 170b may generate a plurality of longitudinal cross-sectional images different from one another by the MPR processing for each of the volume data corresponding to the end-diastole and the volume data corresponding to the end-systole, and identify the contour of the left ventricle of the heart for each of the longitudinal cross-sectional images. The identification function 170b may identify a plurality of contours for each volume data. For example, the identification function 170b may generate the apical four-chamber image and the apical two-chamber image for each volume data, and identify the contour of the left ventricle of the heart for each of the apical four-chamber image and the apical two-chamber image. For another example, the identification function 170b may generate the apical four-chamber image, the apical three-chamber image, and the apical two-chamber image for each volume data, and identify the contour of the left ventricle of the heart for each of the apical four-chamber image, the apical three-chamber image, and the apical two-chamber image.

As described above, the identification function 170b identifies the contour of at least a part of the heart. The identification function 170b identifies the contour of the endocardium of the heart chamber.

The identification function 170b may identify the contour using dictionary data, for example. In the dictionary data, the position of the contour of the left ventricle is registered for each of the types of images such as the apical four-chamber image, the apical three-chamber image, and the apical two-chamber image, for example. For example, in the dictionary data, a position of the contour from the mitral valve to the mitral valve via the cardiac apex in the apical four-chamber image is registered. For another example, in the dictionary data, a position of the contour from the mitral valve to the aortic valve via the cardiac apex in the apical three-chamber image is registered. For another example, in the dictionary data, a position of the contour from the mitral valve to the aortic valve via the cardiac apex in the apical two-chamber image is registered. For example, when the longitudinal cross-sectional image visualizing the left ventricle serving as the target to identify its contour is the apical four-chamber image, the identification function 170b performs, on the apical four-chamber image registered in the dictionary data, the image processing such as deformation and rotation to align the left ventricle visualized in the apical four-chamber image registered in the dictionary data and the left ventricle visualized in the longitudinal cross-sectional image serving as the target to identify its contour. The identification function 170b identifies the contour after the alignment as the result of the deformation and rotation as the contour of the left ventricle serving as the target to identify its contour. The identification function 170b performs the same processing as described above when the longitudinal cross-sectional image visualizing the left ventricle serving as the target to identify its contour is the apical two-chamber image or the apical three-chamber image.

The identification function 170b may identify the contour using a snake method, for example. When using the snake method, the identification function 170b extracts the contour by correcting the shape of a curve in the longitudinal cross-sectional image visualizing the left ventricle serving as the target to identify its contour using an energy function representing a linear sum of internal energy and image energy such that the energy function becomes minimum. The identification function 170b may identify the contour using an active shape model method that extracts a contour line using an active contour model.

Figure 5:
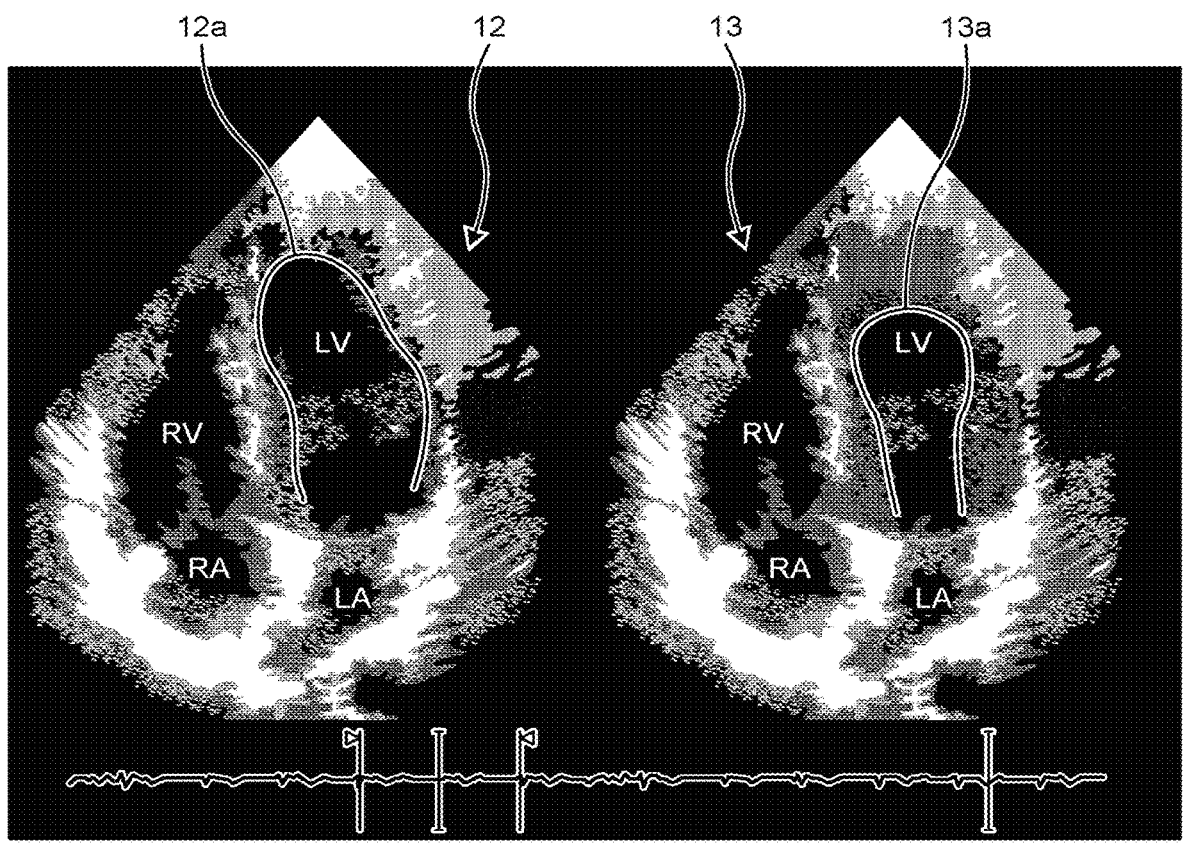
FIG. 5 is a diagram for explaining an example of processing performed by an identification function according to the first embodiment.

FIG. 5 is a diagram for explaining an example of the processing performed by the identification function 170b according to the first embodiment. When the apical four-chamber image 12 and the apical four-chamber image 13 that are exemplarily illustrated in FIG. 4 are selected by the selection function 170a, the identification function 170b identifies a contour 12a of the left ventricle visualized in the apical four-chamber image 12 and a contour 13a of the left ventricle visualized in the apical four-chamber image 13.

As described above, the identification function 170b automatically identifies the contour of the heart without using the speckle tracking at step S106. When the cardiac contour is identified using the speckle tracking, relatively many operations are required as described above. In the first embodiment, the cardiac contour is automatically identified by only the user's single operation of inputting the instruction to automatically calculate the GLS via the input device 102. The single operation is an example of the common operation. The first embodiment, thus, can identify the contour of the myocardium relatively without requiring the user's operation. The ultrasound diagnostic apparatus 1 according to the first embodiment can assist the user to easily perform diagnosis of cardiac diseases.

The control function 140a calculates the GLS serving as a cardiac function parameter representing a myocardial strain using the information about the contour identified by the identification function 170b, and controls the calculation function 170c so as to display the calculated GLS on the display 103 (step S107). At step S107, when the two-dimensional scanning is performed, the calculation function 170c calculates the length L0 of the identified contour in the longitudinal cross-sectional image corresponding to the end-diastole and the length L1 of the identified contour in the longitudinal cross-sectional image corresponding to the end-systole. The calculation function 170c calculates the GLS using the length L0 of the contour and the length L1 of the contour using expression (1).

At step S107, when the three-dimensional scanning is performed, the calculation function 170c calculates the length L0 of the identified three-dimensional contour in the volume data corresponding to the end-diastole and the length L1 of the identified three-dimensional contour in the volume data corresponding to the end-systole. The calculation function 170c calculates the GLS using the length L0 of the contour and the length L1 of the contour using expression (1).

When the three-dimensional scanning is performed and a plurality of contours are identified in each of the volume data corresponding to the end-diastole and the volume data corresponding to the end-systole, two types of methods are available for calculating the GLS.

The following describes one of the two methods. At step S107, the calculation function 170c calculates the lengths of a plurality of contours identified from the volume data corresponding to the end-diastole, and calculates an average of the calculated lengths of the multiple contours as L0. The calculation function 170c also calculates the lengths of a plurality of contours identified from the volume data corresponding to the end-systole, and calculates an average of the calculated lengths of the multiple contours as L1. The calculation function 170c calculates the GLS using L0 and L1 using expression (1).

A specific example of the one method is described. For example, at step S107, the calculation function 170c calculates the lengths of the contour identified in the apical four-chamber image, the contour identified in the apical three-chamber image, and the contour identified in the apical two-chamber image from the volume data corresponding to the end-diastole, and calculates a statistic of the calculated lengths of the three contours, e.g., an average, as L0. The calculation function 170c also calculates the lengths of the contour identified in the apical four-chamber image, the contour identified in the apical three-chamber image, and the contour identified in the apical two-chamber image from the volume data corresponding to the end-systole, and calculates a statistic of the calculated lengths of the three contours, e.g., an average, as L1. The calculation function 170c calculates the GLS using L0 and L1 using expression (1).

The following describes the other one of the two methods. At step S107, the calculation function 170c calculates the lengths of a plurality of contours identified from the volume data corresponding to the end-diastole. The calculation function 170c calculates the lengths of a plurality of contours identified from the volume data corresponding to the end-systole. The calculation function 170c calculates the GLS using expression (1) for each of the multiple contours. The calculation function 170c calculates the GLS for each of a plurality of longitudinal cross-sectional images generated by the MPR from the volume data.

The calculation function 170c calculates the GLS on the basis of the lengths of the identified contour in the same manner as described above.

The control function 140a causes the display 103 to display the GLS (step S108). When a plurality of GLSs are calculated at step S107, the control function 140a causes the display 103 to display the multiple GLSs at step S108.

The control function 140a determines whether an instruction to stop collecting the images including the heart of the subject P is input from the input device 102 by the user operating the input device 102 (step S109). If no instruction to stop collecting the images is input (No at step S109), the processing returns to step S105, from which to step S109, the processing is performed on the next cardiac time phase in the same manner as described above. If the instruction to stop collecting the images is input (Yes at step S109), the control function 140a controls the respective circuitries such that the collection of the images is stopped, and thereafter ends the processing.

As described above, when the time-series volume data (the time-series three-dimensional images generated by the scanning performed on a three-dimensional region) is collected, the identification function 170b of the ultrasound diagnostic apparatus 1 identifies the three-dimensional cardiac contour for each of the three-dimensional image corresponding to the end-systole and the three-dimensional image corresponding to the end-diastole included in the time-series three-dimensional images, and the calculation function 170c calculates the cardiac function parameter using the information about the identified three-dimensional contours.

When the time-series longitudinal cross-sectional images (the time-series two-dimensional images generated by the scanning performed on a two-dimensional region) are collected, the identification function 170b of the ultrasound diagnostic apparatus 1 identifies the two-dimensional cardiac contour for each of the two-dimensional image corresponding to the end-systole and the two-dimensional image corresponding to the end-diastole included in the time-series two-dimensional images, and the calculation function 170c calculates the cardiac function parameter using the information about the identified two-dimensional contours.

The ultrasound diagnostic apparatus 1 according to the first embodiment is described as above. As described above, the control function 140a of the ultrasound diagnostic apparatus 1 causes the selection function 170a to select the images, the identification function 170b to identify the contours, and the calculation function 170c to calculate the GLS by only the user's single operation of inputting the instruction to automatically calculate the GLS. The ultrasound diagnostic apparatus 1 automatically calculates the GLS by only a single operation, in this way. The ultrasound diagnostic apparatus 1, thus, can calculate the GLS relatively without requiring the user's operation. The ultrasound diagnostic apparatus 1, thus, can assist the user to easily perform diagnosis of cardiac diseases.

The calculation of the GLS using the speckle tracking method needs to perform tracking in all of the time phases. As a result, the processing amount is huge. The first embodiment, however, calculates the GLS using the images corresponding to the two time phases. The ultrasound diagnostic apparatus 1 according to the first embodiment, thus, can easily calculate the GLS, which is the cardiac function parameter frequently used as the indicator for quantification of cardiac functions.

First Modification of the First Embodiment

In the first embodiment, when the time-series volume data is collected, the identification function 170b of the ultrasound diagnostic apparatus 1 identifies the three-dimensional cardiac contour for each of the volume data corresponding to the end-systole and the volume data corresponding to the end-diastole included in the time-series volume data, and the calculation function 170c calculates the cardiac function parameter using the information about the identified three-dimensional contours. Although when the time-series volume data is collected, the image generation circuitry 141 of the ultrasound diagnostic apparatus 1 may generate the longitudinal cross-sectional image from each volume data in the time-series volume data by the MPR, and the control function 140a may cause the display 103 to display the longitudinal cross-sectional images in the time-series order at step S101 illustrated in FIG. 2. At step S106, the identification function 170b may identify the two-dimensional cardiac contour for each of the longitudinal cross-sectional image corresponding to the end-systole and the longitudinal cross-sectional image corresponding to the end-diastole included in the time-series longitudinal cross-sectional images, and the calculation function 170c may calculate the GLS using the information about the identified two-dimensional contours at step S107. In the first modification, the user operates the ultrasound probe 101 such that the ultrasound probe 101 scans the apical two-chamber cross section or the apical four-chamber cross section.

Second Modification of the First Embodiment

The ultrasound diagnostic apparatus 1 according to the first embodiment calculates the GLS, which is the cardiac function parameter, using the information about the lengths of the identified contours, and causes the display 103 to display the calculated GLS. The ultrasound diagnostic apparatus 1 may calculate the cardiac function parameters such as the volume of the heart (the volume of the heart chamber) and the ejection fraction of the heart chamber besides the GLS using the information about the lengths of the identified contours, and may cause the display 103 to display the cardiac function parameters such as the volume of the heart and the ejection fraction of the heart chamber. The following describes such an embodiment as a second modification of the first embodiment.

For example, the calculation function 170c according to the second modification calculates, using the identified contours, a volume of the left ventricle formed by the identified contour at the end-systolic (end-systolic volume (ESV)) and a volume of the left ventricle formed by the identified contour at the end-diastolic (end-diastolic volume (EDV)) by a Simpson method or a modified Simpson method.

The following describes an example where the calculation function 170c calculates the volume of the left ventricle using the identified contour by the Simpson method. The calculation function 170c detects the long axis of an inner cavity of the left ventricle formed by the identified contour, for example. The calculation function 170c divides the inner cavity of the left ventricle into a plurality of disks (e.g., 20 disks) perpendicular to the long axis of the left ventricle. The calculation function 170c calculates a distance between two points intersecting the endocardial surface for each of the multiple disks. The calculation function 170c approximates each disk as a columnar slice having a diameter of the calculated distance between the two points. The calculation function 170c calculates a volume of each disk approximated as a columnar slice. The calculation function 170c calculates a sum of the volumes of the respective disks as the volume of the left ventricle.

The following describes an example where the calculation function 170c calculates the volume of the left ventricle using the identified contour by the modified Simpson method. In this case, the apical four-chamber image and the apical two-chamber image are used. The calculation function 170c detects the long axis of an inner cavity of the left ventricle formed by the identified contour in the apical four-chamber image, for example. The calculation function 170c detects the long axis of an inner cavity of the left ventricle formed by the identified contour in the apical two-chamber image. The calculation function 170c divides the inner cavity of the left ventricle formed by the identified contour in the apical four-chamber image into a plurality of disks (e.g., 20 disks) perpendicular to the long axis of the left ventricle (disks in the apical four-chamber image). The calculation function 170c divides the inner cavity of the left ventricle formed by the identified contour in the apical two-chamber image into a plurality of disks (e.g., 20 disks) perpendicular to the long axis of the left ventricle (disks in the apical two-chamber image). The calculation function 170c calculates a distance A between two points intersecting the endocardial surface for each of the multiple disks in the apical four-chamber image. The calculation function 170c calculates a distance B between two points intersecting the endocardial surface for each of the multiple disks in the apical two-chamber image. The calculation function 170c approximates the three-dimensional shape of each disk as an ellipsoidal slice having a major axis estimated from the calculated distance A between two points and a minor axis estimated from the calculated distance B between two points. The calculation function 170c calculates a volume of each disk approximated as an ellipsoidal slice. The calculation function 170c calculates a sum of the volumes of the respective disks as the volume of the left ventricle.

The calculation function 170c calculates the ESV and the EDV as described above. The calculation function 170c calculates the ejection fraction (EF) using the following expression (2).

$$EF=(ESV-EDV)/ESV \qquad (2)$$

Figure 6:
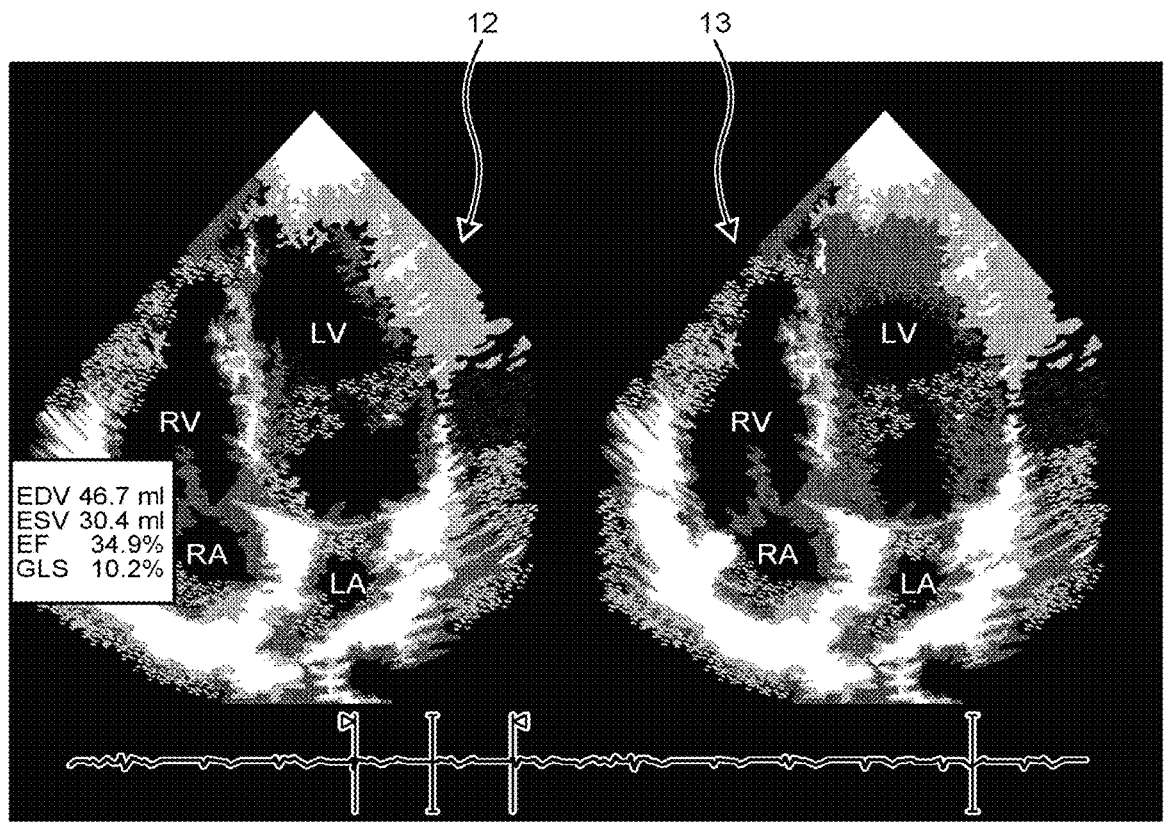
FIG. 6 is a diagram for explaining an example of the processing performed by the ultrasound diagnostic apparatus according to a second modification of the first embodiment.

The control function 140a according to the second modification causes the display 103 to display the ESV, the EDV, and the EF in addition to the GLS. FIG. 6 is a diagram for explaining an example of the processing performed by the ultrasound diagnostic apparatus 1 according to the second modification of the first embodiment. For example, when the calculation function 170c calculates the EDV "46.7 ml", the ESV "30.4 ml", the EF "34.9%", and the GLS "10.2%", the control function 140a causes the display 103 to display the EDV "46.7 ml", the ESV "30.4 ml", the EF "34.9%", and the GLS "10.2%" as exemplarily illustrated in FIG. 6. The control function 140a causes the display 103 to simultaneously display the EDV "46.7 ml", the ESV "30.4 ml", the EF "34.9%", and the GLS "10.2%". The calculation function 170c may calculate at least one of the EDV "46.7 ml", the ESV "30.4 ml", and the EF "34.9%". The calculation function 170c may calculate the cardiac function parameter (first cardiac function parameter) representing at least one of the volume and the ejection fraction of the heart chamber, and the GLS serving as the cardiac function parameter (second cardiac function parameter) representing the global strain of the myocardium corresponding to the heart chamber. The control function 140a may cause the display 103 to display the first cardiac function parameter and the second cardiac function parameter. The control function 140a may cause the display 103 to display the first cardiac function parameter and the second cardiac function parameter by the common operation described above.

The second modification calculates at least one of the volume and the ejection fraction using the already identified contour, thereby making it possible to easily calculate the other cardiac function parameter other than the GLS.

In the second modification, the control function 140a causes the selection function 170a to select the images, the identification function 170b to identify the contours, and controls the display 103 such that the display 103 displays the first cardiac function parameter and the second cardiac function parameter by only the user's single operation of inputting the instruction to automatically calculate the GLS. The ultrasound diagnostic apparatus 1 causes the display 103 to automatically display the first cardiac function parameter and the second cardiac function parameter by only a single operation, in this way. The ultrasound diagnostic apparatus 1 can cause the display 103 to automatically display the first cardiac function parameter and the second cardiac function parameter relatively without requiring the user's operation. The ultrasound diagnostic apparatus 1, thus, can assist the user to easily perform diagnosis of cardiac diseases.

Third Modification of the First Embodiment

The ultrasound diagnostic apparatus 1 according to the first embodiment calculates a single GLS per one cardiac time phase, and causes the display 103 to display the calculated GLS. The ultrasound diagnostic apparatus 1 may calculate the GLS for each of a plurality of cardiac time phases, calculate a statistic of the calculated multiple GLSs, and cause the display 103 to display the calculated statistic of the GLSs. The following describes such an embodiment as a third modification of the first embodiment.

Figure 7:
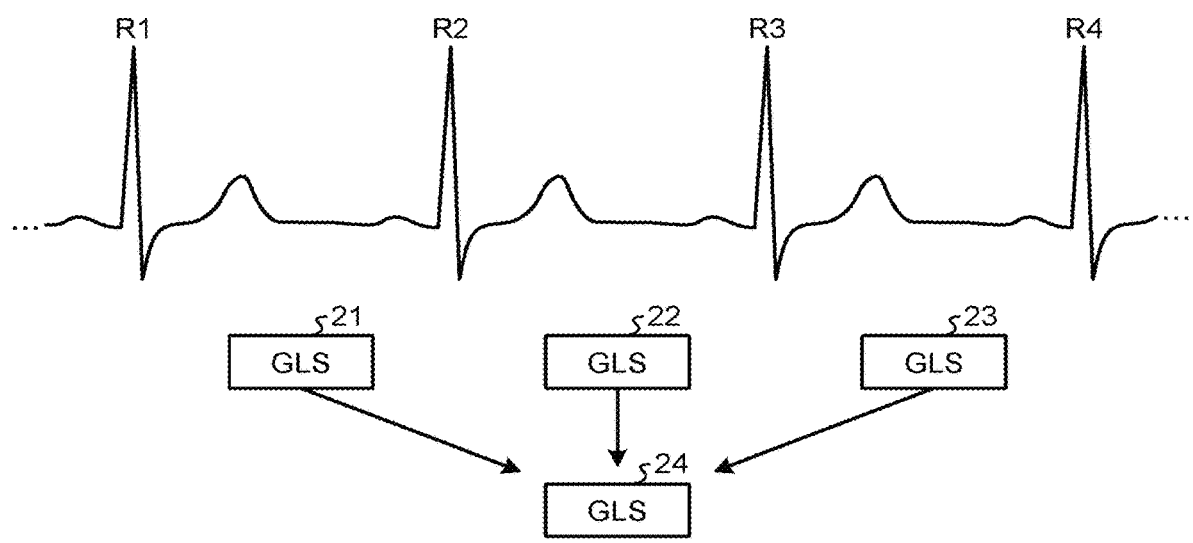
FIG. 7 is a diagram for explaining an example of the processing performed by a calculation function according to a third modification of the first embodiment.

FIG. 7 is a diagram for explaining an example of the processing performed by the calculation function 170c according to the third modification of the first embodiment. FIG. 7 illustrates an exemplary case where the GLS to be displayed on the display 103 is calculated for each of the three cardiac time phases. As exemplarily illustrated in FIG. 7, the calculation function 170c according to the third modification calculates a single GLS per one cardiac time phase in the same manner as the first embodiment. Specifically, the calculation function 170c calculates a GLS 21 between an R wave R1 and an R wave R2. The calculation function 170c calculates a GLS 22 between the R wave R2 and an R wave R3. The calculation function 170c calculates a GLS 23 between the R wave R3 and an R wave R4. The calculation function 170c calculates an average of the GLS 21, the GLS 22, and the GLS 23 as a GLS 24 for the three cardiac time phases. The calculation function 170c causes the display 103 to display the GLS 24. The calculation function 170c updates the GLS displayed on the display 103 every three cardiac time phases.

Although the GLS calculated at a certain cardiac time phase is largely different from those at other cardiac time phases by chance due to the influence of disturbance, for example, the third modification does not cause the display 103 to display the GLS largely different from the others without any change. There is a case where the user performs miss diagnosis when the user sees the GLS largely different from the others, thereby reducing the accuracy in diagnosis result of cardiac diseases. The third modification can prevent the reduction in accuracy in diagnosis result of cardiac diseases by making the user see the extremely different cardiac function parameter.

Fourth Modification of the First Embodiment

Figure 8A:
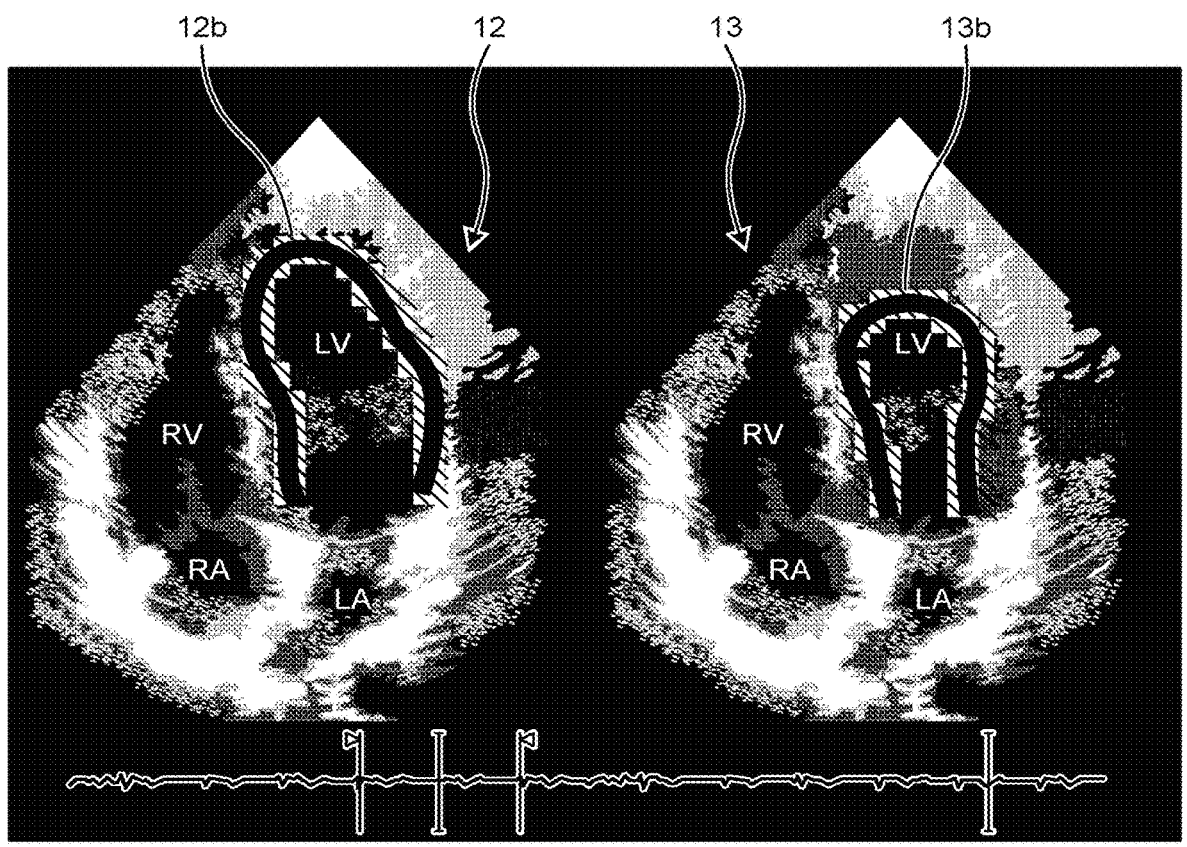
FIG. 8A is a diagram for explaining an example of the processing performed by the control function according to a fourth modification of the first embodiment.

The ultrasound diagnostic apparatus 1 may cause the display 103 to display the identified contours. The following describes such an embodiment as a fourth modification of the first embodiment. FIG. 8A is a diagram for explaining an example of the processing performed by the control function 140a according to the fourth modification of the first embodiment. The following description is based on the case where the contour 12a and the contour 13a are identified by the identification function 170b as exemplarily illustrated in FIG. 5. In this case, as exemplarily illustrated in FIG. 8A, the control function 140a generates an image 12b that represents a shape of a portion anatomically along the myocardium in the contour 12a. The control function 140a generates an image 13b that represents a shape of a portion anatomically along the myocardium in the contour 13a. In the production, when the image 12b overlaps with a portion along the myocardium in the contour 12a in the apical four-chamber image 12, the control function 140a generates the image 12b such that the display form of the portion along the myocardium, i.e., the display form of the image 12b, is differentiated from a portion that is not along the myocardium. For example, the control function 140a generates the image 12b in such a manner that the image 12b is a certain pattern. The control function 140a may generate the image 12b in a color different from that of the portion that is not along the myocardium.

Likewise, when the image 13b overlaps with a portion along the myocardium in the contour 13a in the apical four-chamber image 13, the control function 140a generates the image 13b such that the display form of the portion along the myocardium, i.e., the display form of the image 13b, is differentiated from a portion that is not along the myocardium.

The control function 140a overlaps the generated image 12b with the portion anatomically along the myocardium in the contour 12a in the apical four-chamber image 12 displayed on the display 103. The control function 140a overlaps the generated image 13b with the portion anatomically along the myocardium in the contour 13a in the apical four-chamber image 13 displayed on the display 103. As a result, the control function 140a causes the display 103 to display the image 12b representing the identified contour 12a on the apical four-chamber image 12 in such a manner that the display form of the portion along the myocardium in the identified contour 12a is differentiated from that of the portion that is not along the myocardium. The control function 140a causes the display 103 to display the image 13b representing the identified contour 13a on the apical four-chamber image 13 in such a manner that the display form of the portion along the myocardium in the identified contour 13a is differentiated from that of the portion that is not along the myocardium.

The ultrasound diagnostic apparatus 1 according to the fourth modification can cause the user to easily grasp the shape and the position of the contour serving as the information useful for the diagnosis of cardiac diseases. The ultrasound diagnostic apparatus 1 according to the fourth modification can assist the user to easily perform diagnosis of cardiac diseases.

Figure 8B:
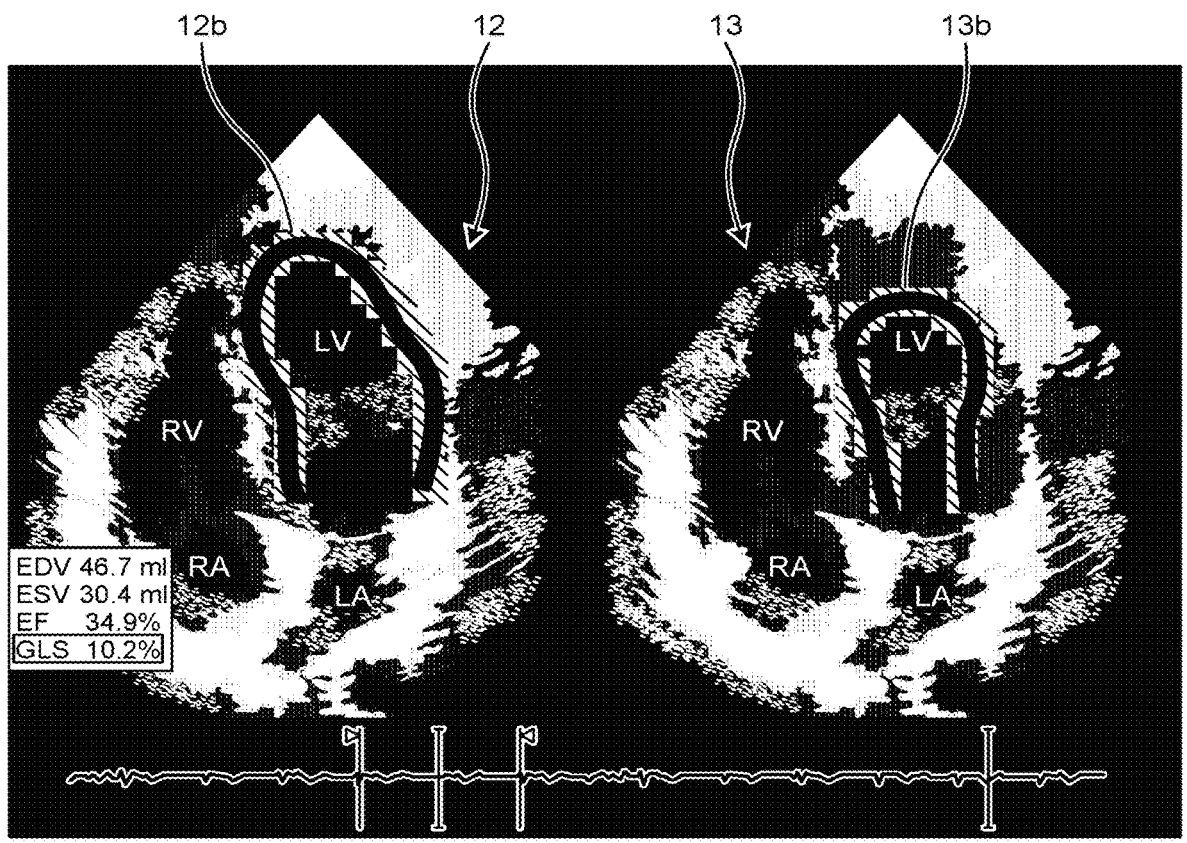
FIG. 8B is a diagram for explaining another example of the processing performed by the control function according to the fourth modification of the first embodiment.

As exemplarily illustrated in FIG. 8B, the control function 140a may display the image 12b on the apical four-chamber image 12 and the image 13b on the apical four-chamber image 13 when the GLS displayed on the display 103 is designated by the user via the input device 102. The control function 140a may display, in accordance with the operation to designate the GLS, the images 12b and 13b each representing a partial contour of the heart serving as the target of the calculation of the designated GLS on the image 12 corresponding to the end-diastole and the image 13 corresponding to the end-systole, respectively. The control function 140a may display, in accordance with the operation to designate the GLS, the image representing a partial contour of the heart serving as the target of the calculation of the designated GLS on at least one of the image 12 corresponding to the end-diastole and the image 13 corresponding to the end-systole. The images 12b and 13b each representing a part of the contour of the heart are examples of the contour marker.

Fifth Modification of the First Embodiment

In the first embodiment, the ultrasound diagnostic apparatus 1 automatically selects the image corresponding to the end-diastole and the image corresponding to the end-systole at step S105 illustrated in FIG. 2, and performs the various types of processing using the selected images. In the first embodiment, the ultrasound diagnostic apparatus 1 automatically identifies the contours at step S106 illustrated in FIG. 2, and performs the various types of processing using the selected contours. The ultrasound diagnostic apparatus 1 may receive the user's designation of the image corresponding to the end-diastole and the image corresponding to the end-systole, and may perform various types of processing using the designated image corresponding to the end-diastole and image corresponding to the end-systole in the same manner as the first embodiment. The ultrasound diagnostic apparatus 1 may receive the trace of the contour from the user, and may perform various types of processing using the traced contour in the same manner as the first embodiment. The following describes such an embodiment as a fifth modification of the first embodiment.

The ultrasound diagnostic apparatus 1 according to the fifth modification does not include the selection function 170a and the identification function 170b. FIG. 9 is a flowchart illustrating an exemplary flow of the processing performed by the ultrasound diagnostic apparatus 1 according to the fifth modification of the first embodiment.

The processing performed from step S101 to step S104 in the flowchart exemplarily illustrated in FIG. 9 is the same as that performed from step S101 to step S104 in the flowchart according to the first embodiment exemplarily illustrated in FIG. 2. The description thereof is, thus, omitted.

As exemplarily illustrated in FIG. 9, at step S201, the control function 140a causes the display 103 to display the longitudinal cross-sectional images out of the longitudinal cross-sectional images that correspond to the certain time period and are acquired from the image memory 150 at step S103 such that the longitudinal cross-sectional image corresponding to the end-diastole and the longitudinal cross-sectional image corresponding to the end-systole can be designated in one cardiac beat when both of the case where the two-dimensional scanning is performed and the case where the three-dimensional scanning is performed.

At step S201, the control function 140a receives the designation of the longitudinal cross-sectional image corresponding to the end-diastole and the longitudinal cross-sectional image corresponding to the end-systole from the user via the input device 102. The longitudinal cross-sectional image corresponding to the end-diastole and the longitudinal cross-sectional image corresponding to the end-systole that are designated at step S201 are used in the various types of processing in the same manner as the first embodiment.

At step S202, the control function 140a causes the display 103 to display the longitudinal cross-sectional image corresponding to the end-diastole and the longitudinal cross-sectional image corresponding to the end-systole that are designated by the user.

At step S202, the control function 140a receives the designation of the traces of the contour at the end-diastole and the contour at the end-systole from the user via the input device 102. The traced contours at the end-diastole and at the end-systole are used in the various types of processing in the same manner as the first embodiment.

The processing performed from step S107 to step S109 in the flowchart exemplarily illustrated in FIG. 9 is the same as that performed from step S107 to step S109 in the flowchart according to the first embodiment exemplarily illustrated in FIG. 2. The description thereof is, thus, omitted. At step S108, the control function 140a may cause the display 103 to display the GLS and the contours, and may receive the correction of the contours from the user via the input device 102. When receiving the correction of the contour, the control function 140a may correct the contour on the basis of the received correction.

The fifth modification is described as above. The ultrasound diagnostic apparatus 1 according to the fifth modification can calculate the GLS although the ultrasound diagnostic apparatus 1 does not include the selection function 170a and the identification function 170b. The ultrasound diagnostic apparatus 1 according to the fifth modification can assist the user to perform diagnosis of cardiac diseases with an inexpensive structure.

Sixth Modification of the First Embodiment

The ultrasound diagnostic apparatus 1 may calculate the other cardiac function parameters besides the GLS, the ESV, the EDV, and the EF. The following describes such an embodiment in which the ultrasound diagnostic apparatus 1 calculates the other cardiac function parameters besides the GLS, the ESV, the EDV, and the EF as a sixth modification of the first embodiment.

In the sixth modification, the ultrasound diagnostic apparatus 1 calculates a moving distance of an annulus between the end-diastole and the end-systole as the cardiac function parameter.

The control function 140a according to the sixth modification controls the identification function 170b such that the identification function 170b identifies a position of the annulus of the mitral valve (annulus position) and a position of the cardiac apex in each of the image corresponding to the end-diastole and the image corresponding to the end-systole, at step S106 illustrated in FIG. 2 in addition to the control described in the first embodiment.

Figure 10:
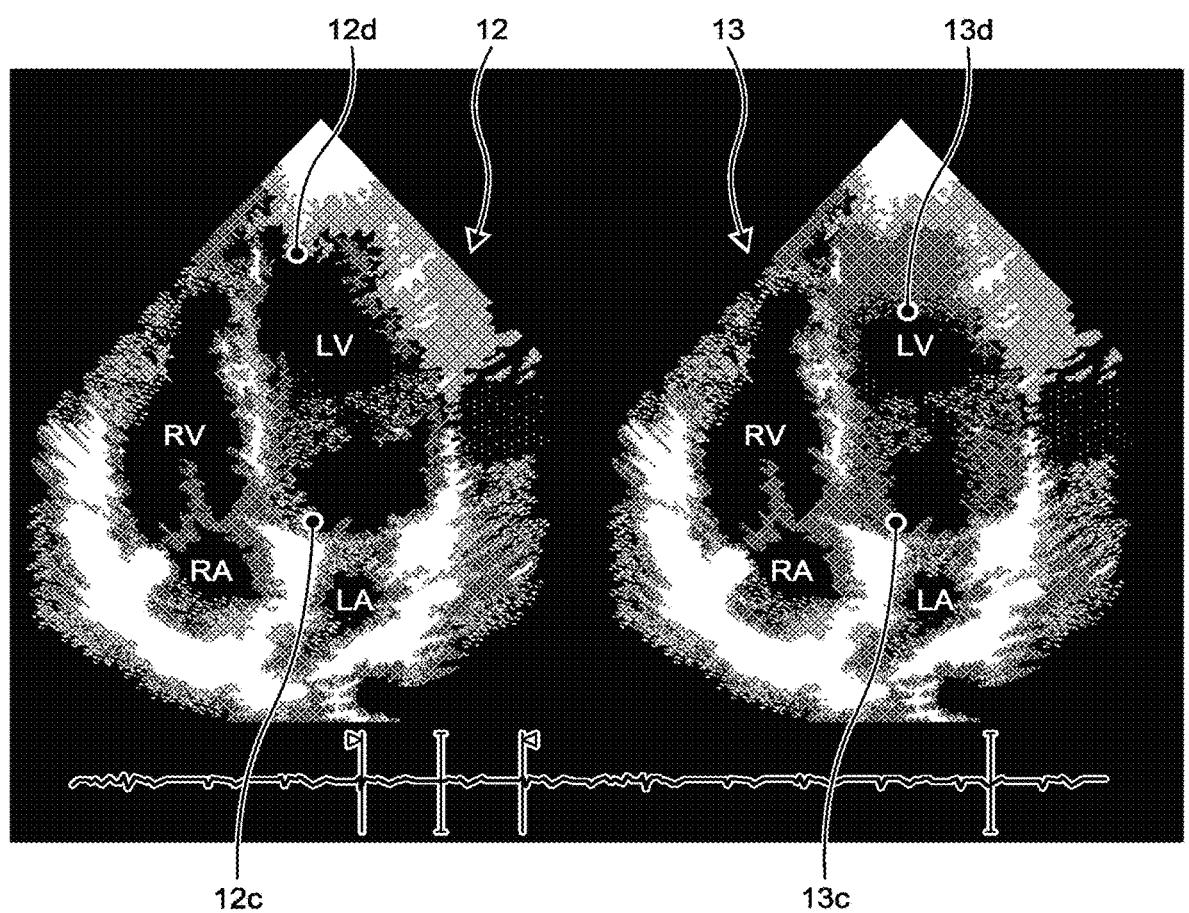
FIG. 10 is a diagram for explaining an example of the processing performed by the identification function and the calculation function according to a sixth modification of the first embodiment.

FIG. 10 is a diagram for explaining an example of the processing performed by the identification function 170b and the calculation function 170c according to the sixth modification of the first embodiment. As exemplarily illustrated in FIG. 10, the identification function 170b identifies an annulus position 12c of the mitral valve in the apical four-chamber image 12 corresponding to the end-diastole at step S106. At step S106, the identification function 170b identifies a position 12d of the cardiac apex in the apical four-chamber image 12 corresponding to the end-diastole.

As exemplarily illustrated in FIG. 10, the identification function 170b identifies an annulus position 13c of the mitral valve in the apical four chamber image 13 corresponding to the end-systole at step S106. At step S106, the identification function 170b identifies a position 13d of the cardiac apex in the apical four-chamber image 13 corresponding to the end-systole.

At step S107 illustrated in FIG. 2, the control function 140a controls the calculation function 170c such that the calculation function 170c calculates a moving distance of the annulus between the end-diastole and the end-systole as the cardiac function parameter in addition to the control described in the first embodiment or any of the modifications described above. At step S107, the calculation function 170c calculates a moving distance of the annulus.

As exemplarily illustrated in FIG. 10, the calculation function 170c calculates a distance (distance d1) between the identified annulus position 12c of the mitral valve and the identified position 12d of the cardiac apex in the apical four-chamber image 12 corresponding to the end-diastole. The calculation function 170c calculates a distance (distance d2) between the identified annulus position 13c of the mitral valve and the identified position 13d of the cardiac apex in the apical four-chamber image 13 corresponding to the end-systole. The calculation function 170c calculates a value obtained by subtracting the distance d2 from the distance d1 as the moving distance of the annulus of the mitral valve.

The moving distance of the annulus is the cardiac function parameter representing a cardiac strain and is the information useful for diagnosis of cardiac diseases.

The ultrasound diagnostic apparatus 1 according to the sixth modification of the first embodiment is described as above. As described above, the control function 140a according to the sixth modification causes the identification function 170b to identify the annulus position, and the calculation function 170c to calculate the moving distance of the annulus in addition to cause the selection function 170a to select the images, the identification function 170b to identify the contours, and the calculation function 170c to calculate the GLS by only the user's single operation of inputting the instruction to automatically calculate the GLS. The ultrasound diagnostic apparatus 1 automatically calculates the moving distance of the annulus in addition to the calculation of the GLS by only a single operation. The ultrasound diagnostic apparatus 1, thus, can calculate the moving distance of the annulus and the GLS relatively without requiring the user's operation. The ultrasound diagnostic apparatus 1, thus, can assist the user to easily perform diagnosis of cardiac diseases.

The identification function 170b according to the sixth modification may identify the annulus positions of the two mitral valves visualized in each of the apical four-chamber image corresponding to the end-diastole and apical four-chamber image corresponding to the end-systole, at step S106. In this case, at step S107, the calculation function 170c may calculate a distance (distance d3) between the identified annulus positions of the two mitral valves in the apical four-chamber image corresponding to the end-diastole, and a distance (distance d4) between the identified annulus positions of the two mitral valves in the apical four-chamber image corresponding to the end-systole. The calculation function 170c may calculate a value obtained by subtracting the distance d4 from the distance d3 as the moving distance of the annulus of the mitral valve.

At step S106, the identification function 170b according to the sixth modification may identify the annulus position of the mitral valve and an annulus position of the aortic valve visualized in each of the apical two-chamber image corresponding to the end-diastole and the apical two-chamber image corresponding to the end-systole. In this case, at step S107, the calculation function 170c may calculate a distance (distance d5) between the identified annulus position of the mitral valve and the identified annulus position of the aortic valve in the apical two-chamber image corresponding to the end-diastole, and a distance (distance d6) between the identified annulus position of the mitral valve and the identified annulus position of the aortic valve in the apical four-chamber image corresponding to the end-systole. The calculation function 170c may calculate a value obtained by subtracting the distance d6 from the distance d5 as the moving distance of the annulus of the mitral valve.

The identification function 170b according to the sixth modification may identify the annulus positions of the two mitral valves and the position of the cardiac apex visualized in each of the apical four-chamber image corresponding to the end-diastole and the apical four-chamber image corresponding to the end-systole, at step S106. In this case, at step S107, the calculation function 170c may calculate distances (distances d7 and d8) between the identified position of the cardiac apex and the respective identified annulus positions of the two mitral valves in the apical four-chamber image corresponding to the end-diastole, and distances (distances d9 and d10) between the identified position of the cardiac apex and the respective identified annulus positions of the two mitral valves in the apical four-chamber image corresponding to the end-systole. The calculation function 170c may calculate a value obtained by subtracting the average of the distances d9 and d10 from the average of the distances d7 and d8 as the moving distance of the annulus of the mitral valve.

At step S106, the identification function 170b according to the sixth modification may identify the annulus position of the mitral valve, and the annulus position of the aortic valve, and the position of the cardiac apex visualized in each of the apical two-chamber image corresponding to the end-diastole and the apical two-chamber image corresponding to the end-systole. In this case, at step S107, the calculation function 170c may calculate a distance (distance d11) between the identified annulus position of the mitral valve and the identified position of the cardiac apex, and a distance (distance d12) between the identified annulus position of the aortic valve and the identified position of the cardiac apex in the apical two-chamber image corresponding to the end-diastole. The calculation function 170c may calculate a distance (distance d13) between the identified annulus position of the mitral valve and the identified position of the cardiac apex, and a distance (distance d14) between the identified annulus position of the aortic valve and the identified position of the cardiac apex in the apical two-chamber image corresponding to the end-systole. The calculation function 170c may calculate a value obtained by subtracting the average of the distances d13 and d14 from the average of the distances d11 and d12 as the moving distance of the annulus of the mitral valve.

Seventh Modification of the First Embodiment

In the first embodiment, if the control function 140a determines that the GLS calculation instruction is input at step S104, the processing from step S105 to step S108 is repeated until it is determined that the instruction to stop the collection is input at step S109. When the control function 140a acquires diagnosis items in the inspection at step S101 and determines that the images collected at step S101 are the images including the heart, i.e., determines that the inspection is performed on the heart, the processing at step S104 may be omitted and the processing at step S105 may be performed after the processing at step S103 has been performed.

In this case, the control function 140a according to the seventh modification causes the selection function 170a to select the images, the identification function 170b to identify the contours, and the calculation function 170c to calculate the GLS without the operation via the input device 102. The ultrasound diagnostic apparatus 1 according to the seventh modification automatically calculates the GLS without the operation. The ultrasound diagnostic apparatus 1 according to the seventh modification can calculate the GLS substantially without the user's operation. The ultrasound diagnostic apparatus 1, thus, can assist the user to easily perform diagnosis of cardiac diseases.

When the seventh modification and the sixth modification are combined, the control function 140a according to the sixth modification causes the identification function 170b to identify the annulus position, and the calculation function 170c to calculate the moving distance of the annulus in addition to cause the selection function 170a to select the images, the identification function 170b to identify the contours, and the calculation function 170c to calculate the GLS without the operation via the input device 102. The ultrasound diagnostic apparatus 1 automatically calculates the moving distance of the annulus in addition to the calculation of the GLS without the operation. The ultrasound diagnostic apparatus 1, thus, can calculate the GLS and the moving distance of the annulus substantially without requiring the user's operation. The ultrasound diagnostic apparatus 1, thus, can assist the user to more easily perform diagnosis of cardiac diseases.

Eighth Modification of the First Embodiment

The calculation function 170c may calculate the GLS by a method different from that described in the first embodiment. The following describes such an embodiment in which the calculation function 170c calculates the GLS by a method different from that described in the first embodiment as an eighth modification of the first embodiment.

For example, at step S107, the calculation function 170c according to the eighth modification divides the contour identified by the identification function 170b into a plurality of segments to determine a plurality of regional portions in the myocardium. For example, the calculation function 170c divides the three-dimensional contour into 18 segments to determine 18 regional portions in the myocardium. The calculation function 170c divides the two-dimensional contour into two segments to determine two regional portions in the myocardium, for example.

The calculation function 170c calculates a strain of the myocardium in the regional portion in the longitudinal direction for each of the multiple regional portions. The calculation function 170c calculates a length L2 of the contour at the end-diastole for each regional portion, for example. The calculation function 170c calculates a length L3 of the contour at the end-systole for each regional portion, for example. The calculation function 170c calculates a strain "Regional Longitudinal Strain" (RLS) of the myocardium in the regional portion in the longitudinal direction for each of the multiple regional portions using expression (3).

$$RLS\ (\%)=[(L3-L2)/L2]*100 \qquad (3)$$

The calculation function 170c calculates a statistic of the calculated strains as the cardiac function parameter. For example, the calculation function 170c may calculate an average of the RLSs each of which is the strain of the myocardium in the regional portion in the longitudinal direction, as the cardiac function parameter of the myocardium, and may cause the display 103 to display the average of the RLSs each of which is the strain of the myocardium in the regional portion in the longitudinal direction.

The user may operate the input device 102 so as to divide the contour at the end-diastole and the contour at the end-systole into a plurality of segments. In this case, the control function 140a may cause the display 103 to display the average of the RLSs, each of which is the strain of the myocardium in the regional portion in the longitudinal direction, and the multiple segments set by the user such that they can be corrected by the user. When receiving the correction from the user, the control function 140a may correct the segments on the basis of the received content of the correction. The calculation function 170c may calculate again the average of the RLSs using the segments after the correction. The display 103 may display the average of the RLSs.

Ninth Modification of the First Embodiment

At step S101, the image generation circuitry 141 of the ultrasound diagnostic apparatus 1 may generate only the image corresponding to the end-diastole and the image corresponding to the end-systole as the time-series images. The following describes such an embodiment as a ninth modification of the first embodiment. When the two-dimensional scanning is performed, at step S101, the image generation circuitry 141 according to the ninth modification generates, as the time-series images, only the longitudinal cross-sectional image corresponding to the end-diastole and the longitudinal cross-sectional image corresponding to the end-systole on the basis of the electrocardiogram from the electrocardiograph 104. When the three-dimensional scanning performed, at step S101, the image generation circuitry 141 generates, as the time-series images, only the volume data corresponding to the end-diastole and the volume data corresponding to the end-systole on the basis of the electrocardiogram from the electrocardiograph 104.

In the processing from step S105 to step S108, the image corresponding to the end-diastole and the image corresponding to the end-systole are used. The other images are not used in the processing from step S105 to step S108 although they are generated. The ninth modification prevents the production of unnecessary images, thereby making it possible to calculate the GLS more easily.

Tenth Modification of the First Embodiment

The transmission-reception circuitry 110 may control the ultrasound probe 101 such that the ultrasound probe 101 performs multi-cross-section scanning, which is a scanning method scanning a number of a plurality of cross sections. The following describes such an embodiment as a tenth modification of the first embodiment.

The multi-cross-section scanning includes simultaneous multi-cross-section scanning that collects images of a number of cross sections at substantially the same timing, and scanning that scans a certain cross section for a certain number of times and thereafter scans another cross section for a certain number of times. Examples of the multi-cross-section scanning include two-cross-section scanning that scans two cross sections and three-cross-section scanning that scans three cross sections. The following describes an example where the ultrasound probe 101 according to the tenth modification performs the three-cross-section scanning that scans the apical four-chamber cross section, the apical three-chamber cross section, and the apical two-chamber cross section as the multi-cross-section scanning. The multi-cross-section scanning performed by the ultrasound probe 101 is not limited to the three-cross-section scanning. The ultrasound probe 101 may perform other multi-cross-section scanning.

At step S101, the control function 140a according to the tenth modification controls the transmission-reception circuitry 110 such that the transmission-reception circuitry 110 causes the ultrasound probe 101 to start the three-cross-section scanning to scan the apical four-chamber cross section, the apical three-chamber cross section, and the apical two-chamber cross section, and starts producing the reflected wave data by performing the various types of processing on the received reflected wave signals. At step S101, the image generation circuitry 141 sequentially generates the apical four-chamber images, the apical three-chamber images, and the apical two-chamber images, and starts sequentially storing the apical four-chamber images, the apical three-chamber images, and the apical two-chamber images in the image memory 150. At step S101, the control function 140a causes the display 103 to display the apical four-chamber images, the apical three-chamber images, and the apical two-chamber images that are stored in the image memory 150 in the time-series order.

At step S105, the control function 140a controls the selection function 170a such that the selection function 170a selects, out of the apical four-chamber images, the apical three-chamber images, and the apical two-chamber images that correspond to a certain time period and are acquired from the image memory 150, the apical four-chamber image corresponding to the end-diastole, the apical three-chamber image corresponding to the end-diastole, and the apical two-chamber image corresponding to the end-diastole, and the apical four-chamber image corresponding to the end-systole, the apical three-chamber image corresponding to the end-systole, and the apical two-chamber image corresponding to the end-systole, in one cardiac beat. As a result, the selection function 170a selects six images of the apical four-chamber image corresponding to the end-diastole, the apical three-chamber image corresponding to the end-diastole, and the apical two-chamber image corresponding to the end-diastole, and the apical four-chamber image corresponding to the end-systole, the apical three-chamber image corresponding to the end-systole, and the apical two-chamber image corresponding to the end-systole, in one cardiac beat.

At step S105, the control function 140a causes the display 103 to display the selected six images.

At step S106, the control function 140a controls the identification function 170b such that identification function 170b automatically traces and identifies the two-dimensional contour of the heart for each of the selected six images. The identification function 170b identifies the contour for each of the selected six images.

At step S107, the control function 140a controls the calculation function 170c such that the calculation function 170c calculates the GLS using the information about the contours identified by the identification function 170b, and causes the calculated GLS to be displayed on the display 103. The calculation function 170c calculates the lengths of the three contours each identified in the apical four-chamber image corresponding to the end-diastole, the apical three-chamber image corresponding to the end-diastole, and the apical two-chamber image corresponding to the end-diastole, and calculates a statistic of the calculated lengths of the three contours, e.g., an average, as L0. The calculation function 170c calculates the lengths of the three contours each identified in the apical four-chamber image corresponding to the end-systole, the apical three-chamber image corresponding to the end-systole, and the apical two-chamber image corresponding to the end-systole, and calculates a statistic of the calculated lengths of the three contours, e.g., an average, as L1. The calculation function 170c calculates the GLS using L0 and L1 using expression (1). The calculation function 170c causes the display 103 to display the calculated GLS.

In the tenth modification, the ultrasound probe 101 scans a plurality of cross sections by the multi-cross-section scanning under the control of the transmission-reception circuitry 110. The user may operate the ultrasound probe 101 such that the ultrasound probe 101 scans a plurality of cross sections by the multi-cross-section scanning. For example, the user may operate the ultrasound probe 101 such that the ultrasound probe 101 scans the apical four-chamber cross section, the apical three-chamber cross section, and the apical two-chamber cross section.

Eleventh Modification of the First Embodiment

The user who has checked the GLS displayed on the display 103 may want to check the RLS of the subject P for inspecting the heart of the subject P further in detail in some cases. The following describes such an embodiment in which the RLS is calculated and displayed after the calculation and display of the GLS as an eleventh modification of the first embodiment.

In the eleventh modification, the control function 140a or the identification function 170b reads, from the internal memory circuitry 160, the information (e.g., the positions of the contours in the images) about the contours (the contours identified by the identification function 170b) used when the GLS is calculated, after the GLS is calculated and displayed, for example. The internal memory circuitry 160 may store therein at least the information about the contour identified in the image corresponding to the end-diastole.

The control function 140a or the identification function 170b reads the information about the contours from the internal memory circuitry 160 when the user operates the input device 102 and the instruction to calculate the RLS is input to the input device 102, for example. The control function 140a or the identification function 170b reads the information about the contours from the internal memory circuitry 160 in accordance with the operation performed after the GLS is displayed. The control function 140a or the identification function 170b reads the information about the contours from the internal memory circuitry 160 in accordance with the operation performed subsequently after the common operation.

The calculation function 170c calculates the RLS, which is a third cardiac function parameter that represents a regional strain of the myocardium corresponding to the heart chamber, using the read information about the contours. The control function 140a causes the display 103 to display the calculated RLS. The calculation function 170c calculates the RLS after the calculation of the GLS, and the control function 140a causes the display 103 to display the calculated RLS.

The following describes a case where the ultrasound diagnostic apparatus calculates the GLS by executing routine inspection software in a routine inspection and calculates the RLS by executing non-routine inspection software in a non-routine inspection performed sequentially after the routine inspection. When there is a lack in cooperation between the routine inspection software and the non-routine inspection software, the processing to identify the contours is performed again in calculating the RLS by the non-routine inspection software although the contours have been identified in calculating the GLS by the routine inspection software. It is, thus, difficult to easily calculate the RLS.

In the eleventh modification, the information about the already identified contours is used in calculating the RLS without performing the processing to identify the contours. The eleventh modification reuses, in the non-routine inspection, the information about the contours identified in the routine inspection. The eleventh modification can easily calculate the RLS.

Twelfth Modification of the First Embodiment

In the eleventh modification, the ultrasound diagnostic apparatus 1 may identify the contours by the speckle tracking, calculate the GLS using the information about the identified contours, and thereafter may calculate the RLS reusing the information about the contours used in calculating the GLS. The following describes such an embodiment as a twelfth modification of the first embodiment.

In the twelfth modification, the identification function 170b identifies a contour of at least a part of the heart for each of a plurality of images (e.g., all of the images) included in the time-series images including the heart of the subject P by the speckle tracking so as to select the image corresponding to the end-systole and the image corresponding to the end-diastole. The images used for identifying the contours are three or more images, for example. The identification function 170b stores the information about the identified contour in the internal memory circuitry 160 for each of the multiple images. The internal memory circuitry 160 stores therein the information about the identified contour for each of the multiple images. The internal memory circuitry 160 may store therein at least the information about the contour identified in the image corresponding to the end-diastole.

The control function 140a or the identification function 170b reads the information about the contour stored in the internal memory circuitry 160 for each of the images.

The identification function 170b identifies again the contour of at least a part of the heart for each of the images by the speckle tracking using the read information about the contour.

The calculation function 170c calculates again the RLS using the information about the contours identified by the speckle tracking. The calculation function 170c calculates the RLS using the information about the contour identified in the image corresponding to the end-systole and information about the contour identified in the image corresponding to the end-diastole out of the images, for example.

Second Embodiment

The functions described in the first embodiment are applicable to an image processing apparatus beside the ultrasound diagnostic apparatus 1, for example.

Figure 11:
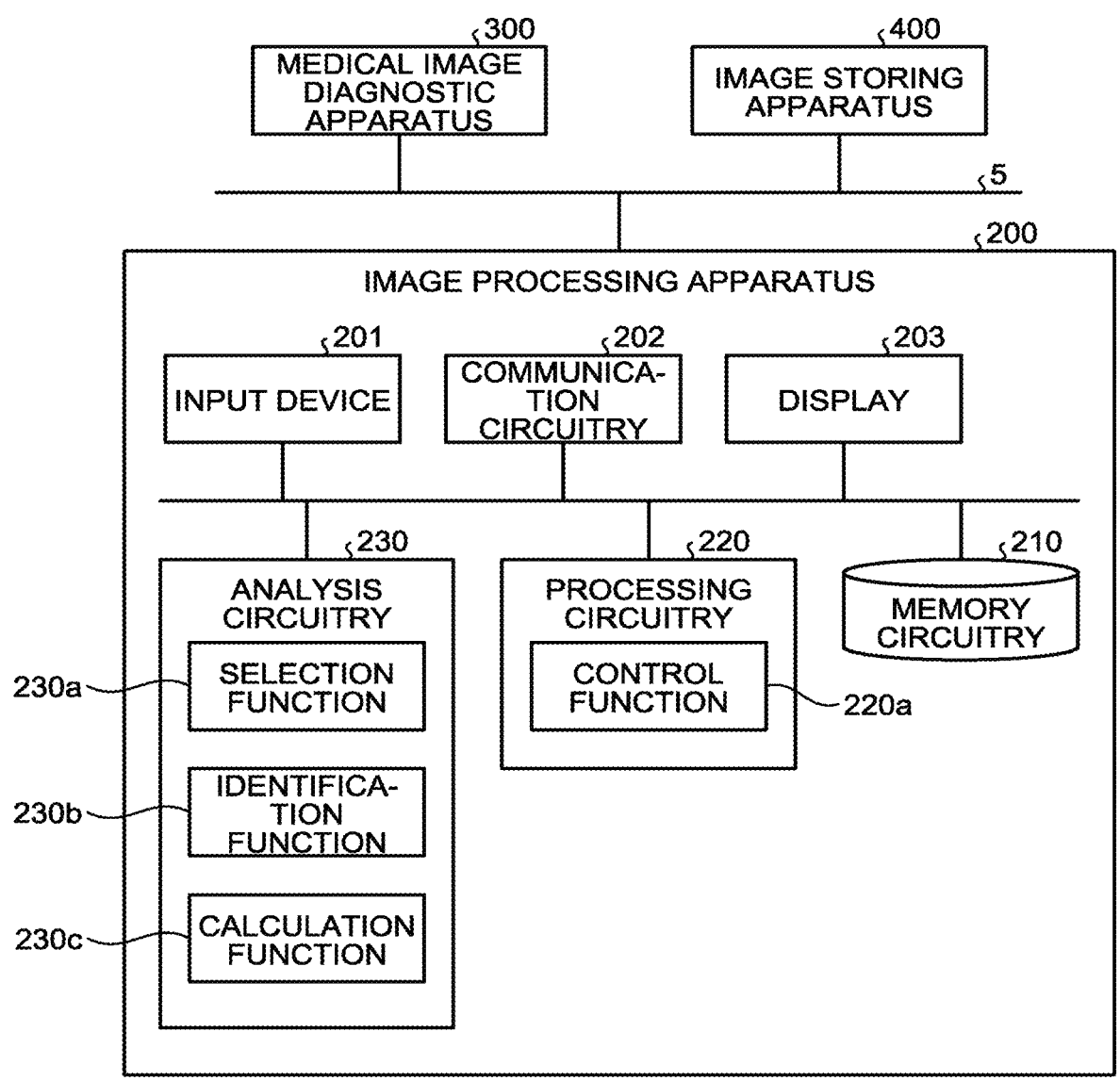
FIG. 11 is a schematic diagram illustrating an exemplary structure of an image processing system according to a second embodiment.

FIG. 11 is a schematic diagram illustrating a structural example of an image processing system according to a second embodiment. As illustrated in FIG. 11, the image display processing system according to the second embodiment includes an image processing apparatus 200, a medical image diagnostic apparatus 300, and an image storing apparatus 400. The respective apparatuses exemplarily illustrated in FIG. 11 can communicate directly or indirectly among them via an in-hospital local area network (LAN) 5 installed in a hospital, for example. For example, when a picture archiving and communication system (PACS) is introduced to the image processing system, the respective apparatuses transmit and receive medical image data among them in conformity with the digital imaging and communications in medicine (DICOM) standard.

In FIG. 11, the medical image diagnostic apparatus 300 stores medical images including the hearts of subjects in the image storing apparatus 400, for example. The medical image diagnostic apparatus 300 is the ultrasound diagnostic apparatus 1, an X-ray diagnostic apparatus, an X-ray computed tomography (CT) apparatus, a magnetic resonance imaging (MRI) apparatus, a single photon emission computed tomography (SPECT) apparatus, a positron emission tomography (PET) apparatus, an SPECT-CT apparatus in which the SPECT apparatus and the X-ray CT apparatus are integrated, a PET-CT apparatus in which the PET apparatus and the X-ray CT apparatus are integrated, a PET-MRI apparatus in which the PET apparatus and the MRI apparatus are integrated, or an apparatus group including a plurality of apparatuses described above, for example.

The image storing apparatus 400 is a database that stores therein medical images. Specifically, the image storing apparatus 400 puts and stores various medical images generated by the medical image diagnostic apparatus 300 in a storage unit. The medical images are each stored in the image storing apparatus 400 in such a manner that the medical image and supplementary information such as a patient ID, an inspection ID, an apparatus ID, and a series ID in association with one another, for example.

The image processing apparatus 200 is a work station or a personal computer (PC), which is used by doctors and laboratory technicians who work in a hospital for browsing the medical images, for example. Operators of the image processing apparatus 200 acquire necessary medical images from the image storing apparatus 400 by performing searches using the patient IDs, the inspection IDs, the apparatus IDs, and the series IDs, for example. The image processing apparatus 200 may receive the medical images directly from the medical image diagnostic apparatus 300. The image processing apparatus 200 is an example of the analyzer.

The image processing apparatus 200 includes an input device 201, communication circuitry 202, a display 203, memory circuitry 210, processing circuitry 220 and analysis circuitry 230. The input device 201, the communication circuitry 202, the display 203, the memory circuitry 210, the processing circuitry 220, and the analysis circuitry 230 are connected to one another.

The input device 201, which includes a pointing device such as a mouse or a pen tablet, a keyboard, and a trackball, receives various types of operation input to the image processing apparatus 200 from the operator. When the mouse is used, input can be performed by a mouse wheel. When the pen tablet is used, input can be performed by flick operation or swipe operation. The communication circuitry 202, which is a network interface card (NIC), for example, communicates with another apparatus. The display 203 is a monitor or a liquid crystal display, for example, and displays various types of information.

The memory circuitry 210, which is a hard disk drive or a semiconductor memory, for example, stores therein various types of information. The memory circuitry 210 stores therein a plurality of pieces of processing performed by the processing circuitry 220, for example.

The processing circuitry 220 is achieved by a processor, for example. The processing circuitry 220 controls the whole of the image processing apparatus 200. The processing circuitry 220 includes a control function 220a.

The analysis circuitry 230 includes a selection function 230a, an identification function 230b, and a calculation function 230c.

The control function 220a has the same function as the control function 140a illustrated in FIG. 1. The selection function 230a has the same function as the selection function 170a. The identification function 230b has the same function as the identification function 170b. The calculation function 230c has the same function as the calculation function 170c. The control function 220a, the selection function 230a, the identification function 230b, and the calculation function 230c perform, on the medical images, the same processing as the first embodiment and the respective modifications. The image processing apparatus 200 according to the second embodiment can obtain the same effects as the first embodiment and the respective modifications.

In the embodiments, the components of the apparatuses illustrated in the drawings are functionally conceptual ones, and are not always required to be physically configured as illustrated in the drawings. The specific forms of distributions and integrations of the apparatuses are not limited to those illustrated in the drawings. All or part of the apparatuses can be configured to be functionally or physically distributed or integrated in arbitrary units in accordance with various loads, the usage states, and the like. Furthermore, all or part of the processing functions performed by the respective apparatuses may be implemented by a CPU and a program analyzed and executed by the CPU, or may be implemented as hardware by wired logics.

The various types of processing described in the embodiments and the modifications described above can be achieved by a computer, such as a personal computer or a work station, executing preliminarily prepared programs. The programs can be distributed via a network such as the Internet. The programs can be recorded on a computer readable recording medium such as a hard disk, a flexible disk (FD), a compact disc read only memory (CD-ROM), a magneto-optical (MO) disc, or a digital versatile disc (DVD), and read from the recording medium and executed by the computer.

At least one of the embodiments described above can assist the user to easily perform diagnosis of cardiac diseases.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analyzer, comprising:
processing circuitry configured to
identify at least a part of a contour of a heart of a subject for an image corresponding to a first cardiac time phase that is included in time-series images including the heart of the subject,
identify the at least part of the contour of the heart of the subject for an image corresponding to a second cardiac time phase that is included in time-series images,
calculate, using information indicating positions of the identified contours, a first cardiac function parameter representing at least one of a volume and an ejection fraction of a heart chamber, and a second cardiac function parameter that is different from the first cardiac function parameter, the second cardiac function parameter representing a global strain of a myocardium corresponding to the heart chamber,
select the image corresponding to the first cardiac time phase and the image corresponding to the second cardiac time phase out of the time-series images, and
cause the selection of the images, the identification of the contours, and control for displaying the first cardiac function parameter and the second cardiac function parameter on a display to be performed in accordance with a first request that is a single request and is a request for calculating a cardiac function parameter.

2. The analyzer according to claim 1, further comprising memory circuitry configured to store therein at least information indicating a position of the contour identified in the image corresponding to the second cardiac time phase, wherein
the processing circuitry
reads the information indicating the position of the contour, the information being stored in the memory circuitry, and
calculates a third cardiac function parameter that represents a regional strain of the myocardium using the read information indicating the position of the contour after the second cardiac function parameter is calculated.

3. The analyzer according to claim 2, wherein the processing circuitry
causes the first cardiac function parameter and the second cardiac function parameter to be displayed in accordance with a first request input to the processing circuitry, and
reads the information indicating the position of the contour stored in the memory circuitry in accordance with a second request input to the processing circuitry after the second cardiac function parameter is displayed.

4. The analyzer according to claim 3, wherein the processing circuitry reads the information indicating the position of the contour stored in the memory circuitry in accordance with the second request input to the processing circuitry subsequently after the first request is input to the processing circuitry.

5. The analyzer according to claim 2, wherein
the processing circuitry identifies the contour for each of three or more images included in the time-series images in order to select the image corresponding to the first cardiac time phase and the image corresponding to the second cardiac time phase,
the memory circuitry stores therein the information indicating positions of the identified contour for each of the three or more images, and
the processing circuitry further reads the information indicating the positions of the contour, the information being stored in the memory circuitry, for each of the three or more images.

6. The analyzer according to claim 2, wherein the processing circuitry
identifies at least a part of a contour of the heart for each of a plurality of images included in the time-series images by speckle tracking using the read information, and
calculates the third cardiac function parameter using information indicating positions of the contour identified by the speckle tracking.

7. The analyzer according to claim 2, wherein the memory circuitry stores therein the information indicating the positions of the contour for each cross section corresponding to each of a plurality of images included in the time-series images.

8. The analyzer according to claim 2, wherein
the time-series images are time-series cross-sectional images each corresponding to a longitudinal cross section of the heart of the subject, and
the processing circuitry
identifies a full contour of an endocardium of the heart chamber, and
calculates the second cardiac function parameter on the basis of a length of the identified full contour.

9. The analyzer according to claim 1, wherein the processing circuitry causes a contour marker representing the contour of the part of the heart of the subject, the contour serving as a target of the calculation of the second cardiac function parameter, to be displayed on at least one of the image corresponding to the first cardiac time phase and the image corresponding to the second cardiac time phase, in accordance with a third request.

10. The analyzer according to claim 1, wherein the first cardiac time phase corresponds to an end-systole while the second cardiac time phase corresponds to an end-diastole.

11. The analyzer according to claim 1, wherein the processing circuitry calculates the second cardiac function parameter for each of a plurality of cross sections different from one another, and calculates a statistic of a plurality of calculated second cardiac function parameters.

12. The analyzer according to claim 1, wherein the processing circuitry calculates the second cardiac function parameter for each of a plurality of cardiac periods different from one another, and calculates a statistic of a plurality of calculated second cardiac function parameters.

13. The analyzer according to claim 1, wherein
the time-series images are time-series two-dimensional images generated from time-series three-dimensional images generated by scanning a three-dimensional region, and
the processing circuitry
identifies a two-dimensional contour of the heart of the subject for the two-dimensional image corresponding to the end-systole and the two-dimensional image corresponding to the end-diastole that are included in the time-series two-dimensional images, and
calculates the first cardiac function parameter and the second cardiac function parameter using the information indicating the positions of the identified two-dimensional contours.

14. The analyzer according to claim 1, wherein
the processing circuitry
identifies the contour of the heart of the subject, the heart of the subject being included in a cross-sectional image corresponding to a longitudinal cross section of the heart of the subject, and
causes the identified contour to be displayed on the cross-sectional image displayed on a display while a display form of a portion along a myocardium in the identified contour and a display form of a portion that is not along the myocardium are differentiated from each other.

15. An analyzer, comprising:
processing circuitry configured to
identify a position of an annulus of a heart of a subject for a cross-sectional image corresponding to a first cardiac time phase that is included in time-series cross-sectional images corresponding to a longitudinal cross section of the heart of the subject,
identify a position of the annulus of the heart of a subject for a cross-sectional image corresponding to a second cardiac time phase that is included in the time-series cross-sectional images,
calculate a moving distance of the annulus between the first cardiac time phase and the second cardiac time phase on the basis of the identified positions of the annulus,
select the image corresponding to the first cardiac time phase and the image corresponding to the second cardiac time phase out of the time-series images, and
cause the selection of the images, the identification of the position of the annulus of the heart, and control for displaying the moving distance of the annulus on a display to be performed in accordance with a first request that is a single request and is a request for calculating the moving distance of the annulus.

16. The analyzer according to claim 1, wherein the second cardiac function parameter is a global longitudinal strain (GLS).

* * * * *

UNITED STATES PATENT AND TRADEMARK OFFICE
CERTIFICATE OF CORRECTION

| | | |
|---|---|---|
| PATENT NO. | : 10,813,621 B2 | Page 1 of 1 |
| APPLICATION NO. | : 15/449020 | |
| DATED | : October 27, 2020 | |
| INVENTOR(S) | : Shogo Fukuda et al. | |

It is certified that error appears in the above-identified patent and that said Letters Patent is hereby corrected as shown below:

On the Title Page

Item (71), the Applicant's name is incorrect. Item (71) should read:
-- (71) Applicant: CANON MEDICAL SYSTEMS CORPORATION, Oawara-shi (JP) --

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*